(12) United States Patent
Perregaard et al.

(10) Patent No.: US 6,602,889 B1
(45) Date of Patent: Aug. 5, 2003

(54) 5-HETEROARYL SUBSTITUTED INDOLES

(75) Inventors: Jens Kristian Perregaard, Jaegerspri (DK); Kim Andersen, Virum (DK); Thomas Balle, Copenhagen S (DK)

(73) Assignee: H. Lundbeck A.S., Valby-Copenhagen (DK)

( * ) Notice: Subject to any disclaimer, the term of this patent is extended or adjusted under 35 U.S.C. 154(b) by 0 days.

(21) Appl. No.: 09/623,232

(22) PCT Filed: Mar. 9, 1999

(86) PCT No.: PCT/DK99/00119

§ 371 (c)(1),
(2), (4) Date: Sep. 28, 2000

(87) PCT Pub. No.: WO99/46259

PCT Pub. Date: Sep. 16, 1999

(30) Foreign Application Priority Data

Mar. 9, 1998 (DK) ................................................ 0318/98

(51) Int. Cl.[7] .................. A61K 31/454; A61K 31/4439; C07D 401/14; A61P 25/00
(52) U.S. Cl. ................ 514/318; 514/339; 514/333; 514/323; 514/241; 514/242; 514/247; 514/256; 514/255.05; 514/252.03; 514/183; 546/193; 546/201; 546/256; 546/268.4; 546/274.4; 544/179; 544/180; 544/182; 544/238; 544/333; 544/405
(58) Field of Search .................. 546/193, 256, 546/274.4, 201, 268.4; 514/323, 339, 333, 318

(56) References Cited

U.S. PATENT DOCUMENTS 5,317,103 A 5/1994 Baker et al. ................. 544/367
5,322,851 A * 6/1994 Perregaard ................... 514/323

FOREIGN PATENT DOCUMENTS

| EP | 497512 | * | 8/1992 | |
| EP | 0 497 512 A2 | | 8/1992 | ......... C07D/403/06 |
| EP | WO 92/13856 | * | 8/1992 | |
| WO | WO 92/13856 | | 8/1992 | ......... C07D/417/14 |
| WO | WO 92/15301 | | 9/1992 | ......... A61K/31/445 |
| WO | WO 94/03446 | * | 2/1994 | |

* cited by examiner

Primary Examiner—Evelyn Mei Huang
(74) Attorney, Agent, or Firm—Darby & Darby

(57) ABSTRACT

The present invention relates to compounds having general formula (I) as defined herein, or a pharmaceutically acceptable acid addition salt thereof. The compounds are selective $\alpha_1$-adrenoceptor ligands.

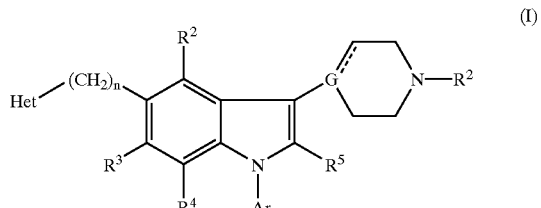

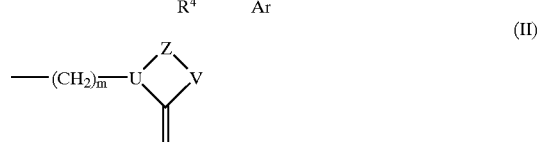

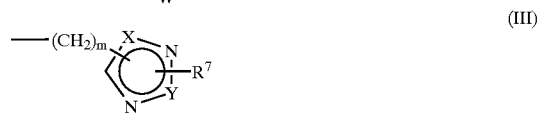

8 Claims, No Drawings

5-HETEROARYL SUBSTITUTED INDOLES

This application is a 371 of PCT/DK99/00119, filed on Mar. 9, 1999.

The present invention relates to novel 5-heteroaryl substituted indoles having high affinity for $\alpha_1$-adrenoceptors. According to their activity at $\alpha_1$-adrenoceptors, the compounds of the invention are considered useful for the treatment of diseases or disorders responsive to $\alpha_1$-adrenoceptor antagonists. Further, as the compounds are selective $\alpha_1$-adrenoceptor ligands they may be particularly useful as PET or SPECT ligands.

BACKGROUND

U.S. Pat. No. 4,710,500 discloses in general optionally 5-substituted indole derivatives having the general formula:

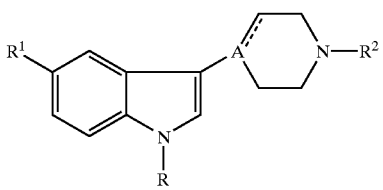

The compounds may be substituted in position 5 with a substituent selected from halogen, lower alkyl, lower alkoxy, hydroxy, cyano, nitro, lower alkylthio, $CF_3$, lower alkylsulphonyl, amino, lower alkylamino and lower di-alkyamino. The compounds are claimed to be potent and long-lasting dopamine antagonists, and accordingly useful for the treatment of psychoses, and additionally to be strong 5-HT antagonists indicating effects in the treatment of negative symptoms of schizophrenia and depression and for the treatment of cardiovascular diseases.

The use of sertindole having the formula

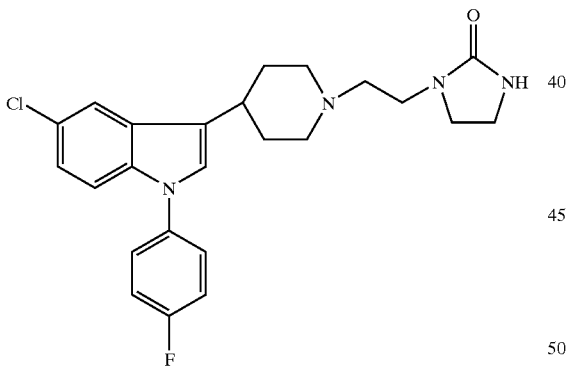

an antipsychotic is specifically claimed in EP-A2-0 392 959.

This type of compounds has also been shown to be useful for the treatment of a range of other disorders including anxiety (WO 92/00070), cognitive disorders (WO 92/15303), abuse (WO 92/15302) and hypertension (WO 92/15301).

WO 92/15301 discloses compounds having affinity for the $\alpha_1$-adrenoceptor. The compounds of the present invention differ from the compounds disclosed therein by being substituted in position 5 with an aromatic heterocyclic ring.

The compounds disclosed in WO 92/15301 are not selective for the $\alpha_1$-adrenoceptor.

Interest in the development of $\alpha_1$-adrenoceptor antagonists has primarily focused on therapeutics for the treatment of Benign Prostatic Hyperplacia (BPH) and cardiovascular diseases (Hieble et al., *Exp. Opin. Invest. Drugs*, 1997, 6, 3657). Prazosin is the prototype of an $\alpha_1$-adrenoceptor antagonist which has very potent peripherally effects. Prazosin has also in some animal models indicated effects in the central nervous system, although prazosin is considered to have poor CNS penetration. Until now, no $\alpha_1$-adrenoceptor selective antagonist with good CNS penetration to the human brain has been described.

Evidence exists indicating that blockade of $\alpha_1$-adrenoceptor neurotransmission could be beneficial in the treatment of schizophrenia. Most classical antipsychotics including clozapine bind potently to $\alpha_1$-adrenoceptors labelled with [$^3$H]prazosin or [$^3$H]WB-4101. Some studies seem to indicate a central role of the $\alpha_1$-component for the atypical profile of clozapine (Baldessarini, et al., *Br. J. Psychiatry*, 1992, 160, 12–16 and Prinssen, et al., *Eur. J. Pharmacol.*, 1994, 262, 167–170). Further, repeated co-administration of prazosin and haloperidol was found to reduce the effect of haloperidol on the firing of dopamine neurons in nigrostriatal areas, suggesting that the combination would be effective as antipsychotic treatment without producing extrapyramidal side effects (EPS) (Chiodo, et al., *J. Neurosci*. 1985, 3, 2539–2544).

It has also been suggested that centrally acting $\alpha_1$-adrenoceptor antagonists will have antimanic effects while corresponding agonists would be beneficial for the treatment of depression (Lipinsky, et al., *Life Sciences*, 1987, 40, 1947–1963).

Labelled compounds of the present invention are considered to be valuable PET (positron emission tomography) ligands and SPECT ligands due to their selectivity for $\alpha_1$-adrenoceptors.

Finally, it is well established that $\alpha_1$-adrenoceptor antagonists acting peripherally are useful for the treatment of benign prostatic hyperplacia, hypertension and cardiac arrhytrnias and for the reduction of intra ocular pressure.

THE INVENTION

Accordingly, the present invention relates to 5-substituted indole derivatives having the general formula:

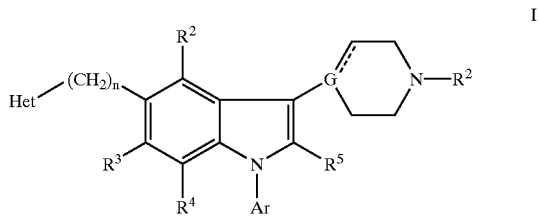

wherein
- Het is a five or six membered aromatic heterocyclic ring containing at least one nitrogen as a ring member, and optionally substituted with one or more substituents selected from $C_{1-6}$-alkyl, $C_{1-6}$-alkoxy, $C_{1-6}$-alkylthio and hydroxy;n is 0, or 1;
- G is N, C, or CH; the dotted line meaning a bond when G is C, and the dotted line meaning no bond when G is CH, or N;
- Ar is phenyl optionally substituted with one or more substituents independently selected from halogen, $C_{1-6}$-alkyl, $C_{1-6}$-alkoxy, hydroxy, trifluoromethyl and cyano, or Ar is 2-thienyl, 3-thienyl, 2-furanyl, 3-furanyl, 2-thiazolyl, 2-oxazolyl, 2-imidazolyl, 2-pyridyl, 3-pyridyl, or 4-pyridyl;
- $R^2$, $R^3$, $R^4$ and $R^5$ are independently selected from hydrogen, $C_{1-6}$-alkyl, $C_{1-6}$-alkoxy, hydroxy, halogen, trifluoromethyl, nitro, cyano, amino, $C_{1-6}$-alkylamino and $C_{1-6}$-dialkylamino;

$R^6$ is hydrogen, $C_{3-8}$-cycloalkyl, $C_{3-8}$-cycloalkyl-$C_{1-6}$-alkyl, $C_{1-6}$-alkyl, or $C_{2-6}$-alkenyl, optionally substituted with one or two hydroxy groups, any hydroxy group present being optionally esterified with an aliphatic carboxylic acid having from two to twentyfour carbon atoms inclusive, or $R^6$ is a group of the formula II or III:

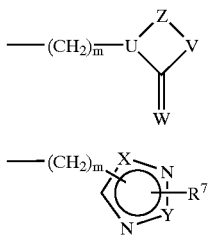

wherein m is an integer from 2–6;
W is O, or S;
U is N or CH;
Z is —$(CH_2)_p$—, p being 2 or 3, or Z is —CH=CH— or 1,2-phenylene optionally substituted with halogen or trifluoromethyl, or Z is —$COCH_2$— or —$CSCH_2$—;
V is O, S, $CH_2$, or $NR^9$, wherein $R^9$ is hydrogen, $C_{1-6}$-alkyl or $C_{2-6}$-alkenyl optionally substituted with one or two hydroxy groups, or a $C_{3-8}$-cycloalkyl or $C_{3-8}$-cycloalkyl-$C_{1-6}$-alkyl group; X is N, C, or CH; Y is N, C, or CH; provided at least one of X and Y is N; and $R^7$ is hydrogen, or $C_{1-6}$-alkyl;

or a pharmaceutically acceptable acid addition salt thereof.

In another aspect, the present invention relates to a pharmaceutical composition comprising at least one compound of formula I as defined above or a pharmaceutically acceptable acid addition salt thereof and optionally a second pharmaceutically active ingredient in combination with one or more pharmaceutically acceptable carriers or diluents.

In a further aspect, the present invention relates to the use of a compound of formula I as defined above or an acid addition salt thereof and optionally a second pharmaceutically active ingredient for the manufacture of a pharmaceutical preparation for the treatment of a disorder or disease responsive to antagonism of $\alpha_1$-adrenoceptor.

Diseases or disorders responsive to antagonism of $\alpha_1$-adrenoceptors includes psychosis, mania, benign prostatic hyperplacia, hypertension, cardiac arrhytmias and reduction of intra ocular pressure.

In still another aspect, the present invention relates to the use of a compound of formula I as above and optionally a second agent having antipsychotic activity for the preparation of a medicament for the treatment of psychosis.

In a further aspect, the invention relates to a method for the treatment of a disorder or disease responsive to antagonism of $\alpha_1$-adrenoceptors in a mammal comprising administering a compound of formula I as above and optionally a second pharmaceutically active ingredient to said mammal.

In still another aspect, the present invention relates to a method for the treatment of psychosis in a mammal comprising administering a compound of formula I as above and optionally a second agent having antipsychotic activity to said mammal.

Finally, the present invention relates to radio-labelled compounds of formula I and the use thereof in various biological assays and PET- or SPECT studies.

DETAILED DESCRIPTION OF THE INVENTION

When used herein halogen means fluoro, chloro, bromo or iodo.

The term $C_{1-6}$ alkyl refers to a branched or unbranched alkyl group having from one to six carbon atoms inclusive, including groups such as methyl, ethyl, 1-propyl, 2-propyl, 1-butyl, 2-butyl, 2-methyl-2-propyl and 2-methyl-1-propyl.

Similarly, $C_{2-6}$ alkenyl designates such groups having from two to six carbon atoms, including one double bond, including groups such as ethenyl, propenyl and butenyl.

The terms $C_{1-6}$ alkoxy, $C_{1-6}$ alkylthio, $C_{1-6}$ alkylamino, $C_{1-6}$ dialkylamino etc. designate such groups in which $C_{1-6}$ alkyl is as defined above.

The term $C_{1-3}$ cycloalkyl designates a monocyclic or bicyclic carbocycle having three to eight C-atoms including such groups as cyclopropyl, cyclopentyl, cyclohexyl, etc.

A five membered aromatic heterocyclic ring containing at least one nitrogen as a ring member, includes, but are not limited to, heterocyclic rings selected from pyrrol-1-yl, pyrrol-2-yl, pyrrol-3-yl, imidazol-1-yl, imidazol-2-yl, imidazol-4-yl, pyrazol-1-yl, pyrazol-3-yl, pyrazol-4-yl, 1,2,3-triazol-1-yl, 1,2,3-triazol-2-yl, 1,2,3-triazol-4-yl, 1,2,4-triazol-1-yl, 1,2,4-triazol-3-yl, 1,24-triazol-5-yl, tetrazol-1-yl, tetrazol-2-yl, tetrazol-5-yl, oxazol-2-yl, oxazol4-yl, oxazol-5-yl, isoxazol-3-yl, isoxazol-4-yl, isoxazol-5-yl, thiazol-2-yl, thiazol-4-yl, thiazol-5-yl, isothiazol-3-yl, isothiazol-4-yl, isothiazol-5-yl, 1,2,3-oxadiazol4-yl, 1,2,3-oxadiazol-5-yl, 1,2,4-oxadiazol-3-yl, 1,2,4-oxadiazol-5-yl, 1,3,4-oxadiazol-2-yl, 1,3,4-oxadiazol-5-yl, 1,2,3-thiadiazol-4-yl, 1,2,3-thiadiazol-5-yl, 1,2,4-thiadiazol-3-yl, 1,2,4-thiadiazol-5-yl, 1,3,4-thiadiazol-2-yl, 1,3,4-thiadiazol-5-yl, 1,2,5-oxadiazol-3-yl, 1,2,5-thiadiazol-3-yl, oxatriazol-4-yl and thiatriazol-4-yl.

A six membered aromatic heterocyclic ring containing at least one nitrogen as a ring member, includes, but are not limited to, pyridin-2-yl, pyridin-3-yl, pyridin4-yl, pyrimidin-2-yl, pyrimidin-4-yl, pyrimidin-5-yl, pyridazine-3-yl, pyridazine-4-yl, pyrazine-2-yl, 1,2,3-triazine-4-yl, 1,2,3-triazine-5-yl, 1,2,4-triazine-3-yl, 1,2,4-triazine-5-yl, 1,2,4-triazine-6-yl, 1,3,5-triazine-2-yl and 1,2,4,5-tetrazine-3-yl.

The acid addition salts of the compounds of the invention are pharmaceutically acceptable salts formed with non-toxic acids. Exemplary of such organic salts are those with maleic, fumaric, benzoic, ascorbic, succinic, oxalic, bis-methylenesalicylic, methanesulfonic, ethanedisulfonic, acetic, propionic, tartaric, salicylic, citric, gluconic, lactic, malic, mandelic, cinnamic, citraconic, aspartic, stearic, palmitic, itaconic, glycolic, p-aminobenzoic, glutamic, benzenesulfonic, and theophylline acetic acids, as well as the 8-halotheophyllines, for example 8-bromotheophylline. Exemplary of such inorganic salts are those with hydrochloric, hydrobromic, sulfuric, sulfamic, phosphoric, and nitric acids.

The selectivity of the compounds of the invention for the $\alpha_1$-adrenoceptor makes them particularly useful for the development of labelled ligands useful in various biological assays and in PET and SPECT studies.

The compounds can be labelled by reacting the unlabelled precursor molecules with [$^{11}$C]methyl iodide, [$^{11}$C]methyl triflate, or other [$^{11}$C] labeled reagents derived from [$^{11}$C] carbon dioxide. The compounds may also be labelled with $^{18}$F or $^{123}$I.

The compounds of the present invention can be prepared according to the procedures described below:

a) Reacting an indole derivative of the following formula

IV wherein $R^2$, $R^3$, $R^4$, $R^5$, Ar, Het and n are as defined above, with a 4-piperidinone of the formula wherein $R^6$ is as defined above, A is an oxo group, or a —O—$(CH_2)_q$—O— chain, wherein q is 2, or 3;

b) reducing the tetrahydropyridine double bond in a compound of the formula

VI wherein $R^2$, $R^3$, $R^4$, $R^5$, $R^6$, Ar, Het and n are as defined above;

c) reacting a compound of the formula

VII wherein $R^2$, $R^3$, $R^4$, $R^5$, $R^6$, G, the dotted line, Het and n are as defined above, with a compound of the formula Ar-hal wherein Ar is as defined above and "hal" is halogen, in the presence of a metal catalyst, d) reacting a compound of the formula

VIII wherein $R^2$, $R^3$, $R^4$, $R^5$, G, the dotted line, Ar, Het and n are as defined above, with $R^9$—L wherein $R^9$ is $C_{3-8}$-cycloalkyl, $C_{3-8}$-acycloalkyl-$C_{1-6}$-alkyl, $C_{1-6}$-alkyl, or $C_{2-6}$-alkenyl and L is halogen, mesylate, or tosylate, or an epoxide of formula wherein R is hydrogen, or $C_{1-4}$-alkyl;

e) reducing the carbonyl group of a compound of the formula

IX wherein $R^2$, $R^3$, $R^4$, $R^5$, G, the dotted line, Ar, Het and n are as defined above and $R^8$ is $C_{3-8}$-cycloalkyl, $C_{1-5}$-alkyl, $C_{3-8}$-cycloalkyl-$C_{1-5}$-alkyl;

f) reacting a compound of the formula

X wherein $R^2$, $R^3$, $R^4$, Ar, Het and n are as defined above, with a piperazine of the formula wherein $k^6$ is as defined above;

g) reducing a compound of the formula

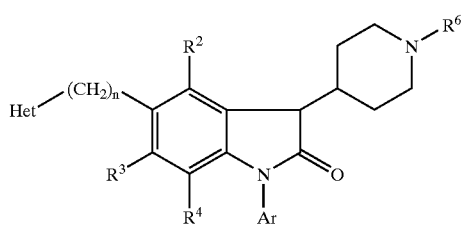

XI wherein $R^2$, $R^3$, $R^4$, $R^6$, Ar, Het and n are as defined above, with a suitable reducing agent;

h) reacting a compound having the formula

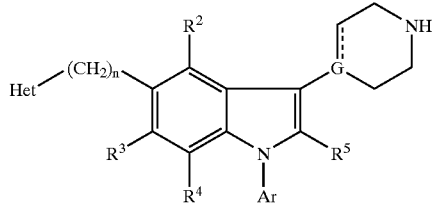

XII wherein $R^2$, $R^3$, $R^4$, $R^5$, G, the dotted line, Ar, Het and n are as defined above with a compound having the formula $L^1$-$R^6$ wherein $R^6$ is a group of formula II or III as defined above and $L^1$ is chloro, bromo, iodo, mesylate, or tosylate;

i) reacting a compound of the formula

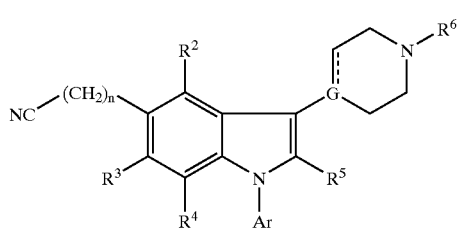

XIII wherein $R^2$, $R^3$, $R^4$, $R^5$, $R^6$, G, the dotted line, Ar and n are as defined above with azide;

j) reacting a compound of the formula

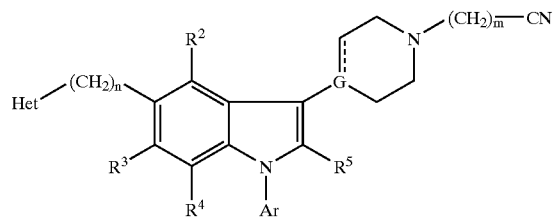

XIV wherein $R^2$, $R^3$, $R^4$, $R^5$, G, the dotted line, Het, Ar, m and n are as defined above with azide;

k) alkylating the group Het, and/or the group of Formula III in a compound of formula I with an alkylating reagent, such as $C_{1-6}$-alkyl-$L^1$, wherein $L^1$ is as defined above;

l) reacting a compound of formula

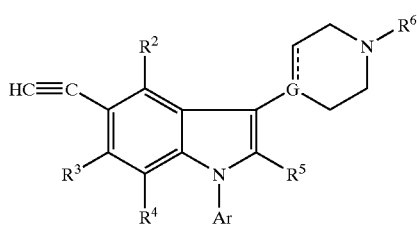

XV wherein $R^2$, $R^3$, $R^4$, $R^5$, $R^6$, G, the dotted line and Ar are as defined above with azidotrimethylsilane;

m) reacting a compound of the formula XVI

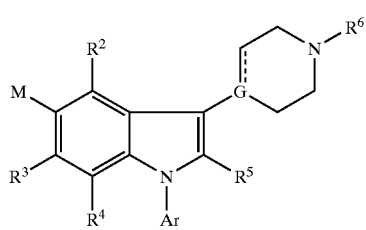

XVI wherein $R^2$, $R^3$, $R^4$, $R^5$, $R^6$, G, the dotted line and Ar are as defined above and M is ZnBr, MgBr, B(OH)$_2$, or Sn(lower alkyl)$_3$ with a compound of the formula Het-V wherein V is Br or I and Het is as defined above; or n) reacting a compound of the formula XVII

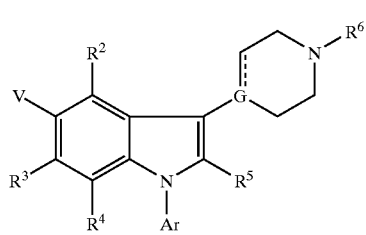

XVII wherein $R^2$, $R^3$, $R^4$, $R^5$, $R^6$, G, the dotted line, Ar and V are as defined above with Het-M wherein Het and M is as defined above:

Methods for the preparation of the starting materials used in the above processes are described in U.S. Pat. No. 4,710,500, WO 92/00070 and in Perregaard et al., *J. Med. Chem.*, 1992 (35), 1092–1101, or can be prepared analogously to the procedures described herein.

Starting materials of formula IV may be prepared by arylation of the corresponding 1-unsubstituted derivatives according to the procedures described in Perregaard et al., *J. Med. Chem.*, 1992 (35), 1092–1101. The 1-unsubstituted derivatives used as starting material for these preparations may be prepared by coupling reactions as outlined in the following.

Starting materials of formula IV in which n is equal to 0 may also be prepared from the corresponding 5-bromo-indoles by means of coupling reactions such as the Stille, Suzuki or Negishi reactions with heteroaryl stannanes, boronic acids or zinc halogenides, respectively, using appropriate catalysts in analogy to literature procedures (Yang et al., Synth. Commun. 1992, (22), 1757–1762; Pearce et al., Synth. Commun. 1992, (22), 1627–1643; Hudkins et al. J. Org. Chem., 1995, (60), 6218–6220, Areadi et al, Synlett, 1990, 47–48; Heterocycles, 1990, (30), 645).

Alternatively, the starting materials of formula IV in which n is equal to 0 may be prepared from the corresponding 5-indolyl stannanes, boronic acids or zinc halogenides by means of coupling reactions such as the Stille, Suzuki or Negishi reactions, respectively, with heteroaryl halogenides of formular Het-Hal, using appropriate catalysts in analogy to literature procedures (Yang et al. Heterocycles 1992 (34), 1395–1398, J. Heterocyclic Chem. 1991 (28), 411).

Starting materials wherein the group Het is tetrazol-5-yl may be prepared by reacting the corresponding 5-cyano-indole with azide (Wentrup et al., J. Am. Chem. Soc. 1984, 106, 3705–6).

Starting materials wherein the group Het-$(CH_2)_n$— is tetrazol-5-ylmethyl may likewise be prepared from the corresponding indole containing a 5-cyanomethyl group by reaction with azide. The 5-cyanomethyl-indoles may be prepared by hydrolysis of the corresponding 5-cyano-indole, reduction of the carboxylic acid functionality obtained to hydroxymethyl, reaction with methanesulphonyl chloride to form the corresponding 5-chloromethyl-indoles followed by reaction with a cyanide to form the 5-cyanomethyl-indole.

Starting materials of the Formula XV may be prepared by reaction of the corresponding 5-bromo-indole compound with (trimethylsilyl)acetylen.

In method a) the reaction is performed under strong acidic conditions at elevated temperature. Trifluoroacetic acid or HCl in ethanol are preferred as acidic catalysts.

In method b) the reduction is preferably carried out at low hydrogen pressures (3 Ato.) in the presence of platinum or palladium on carbon black.

In method c) the arylation is preferably carried out at about 160–210° C. in aprotic polar solvents as e.g. N-methyl-2-pyrrolidinone or hexamethylphosphoric triamide with $K_2CO_3$ as base and copper as a catalyst.

In method e) the reduction is preferably carried out with $LiAlH_4$ in THF or diethylether or with diborane in THF.

Method f) is a two step procedure in which compound X is first decarboxylated in the presence of an inorganic salt as e.g. LiCl or $MgCl_2$ in a polar solvent as e.g. diglyme, hexamethylphosphoric triamide or N-methyl-2-pyrolidone at elevated temperatures (120–150° C.). Finally, the appropriate piperazine is added and the temperature raised to about 200° C. and kept there until the corresponding indoxyle has disappeared according to TLC analysis. The compounds of Formula X are conveniently prepared according to the procedures reported by P. C. Unangst and M. E. Carethers, J. Heterocyclic Chem., 1984, 21, 709

In method g) diborane in THF is conveniently used as reducing agent. The compounds of Formula XI are prepared from the corresponding N-substituted isatins.

The compounds of formula XVI can be prepared from the corresponding 5-halogen substituted indoles.

In the following the invention is further illustrated by way of examples which, however, may not be construed as limiting.

EXPERIMENTAL SECTION

All reactions were carried out under a positive pressure of nitrogen. Melting points were determined on a Buichi SMP-20 apparatus and are uncorrected. Mass spectra were obtained on a Quattro MS-MS system from VG Biotech, Fisons Instruments. The MS-MS system was connected to an HP 1050 modular HPLC system. A volume of 20–50 $\mu$l of the sample (10 $\mu$g/mL) dissolved in a mixture of 1% acetic acid in acetonitril/water 1:1 was introduced via the autosampler at a flow of 30 $\mu$l/mm into the Electrospray Source. Spectra were obtained at two standard sets of operating conditions. One set to obtain molecular weight information (MH+) (21 eV) and the other set to induce fragmentation patterns (70 eV). The background was subtracted. The relative intensities of the ions are obtained from the fragmentation pattern. When no intensity is indicated for the Molecular Ion (MH+), this ion was only present under the first set of operating conditions. 1H NMR spectra were recorded of all novel compounds at 250 MHz on a Bruker AC 250 or at 500 MHz on a Bruker Avance DRX500 instrument. Deuterated chloroform (99.8%D) or dimethyl sulfoxide (99.9%D) were used as solvents. TMS was used as internal reference standard. Chemical shift values are expressed in ppm-values. The following abbreviations are used for multiplicity of NMR signals: s=singlet, d=doublet, t-triplet, q=quartet, qui=quintet, h=heptet, dd=double doublet, dt=double triplet, dq=double quartet, tt=triplet of triplets, m=multiplet. NMR signals corresponding to acidic protons are generally omitted. Content of water in crystalline compounds was determined by Karl Fischer titration. Standard workup procedures refer to extraction with the indicated organic solvent from proper aqueous solutions, drying of combined organic extracts (anhydrous $MgSO_4$ or $Na_2SO_4$), filtering and evaporation of the solvent in vacuo. For column chromatography silica gel of type Kieselgel 60, 230–400 mesh ASTM was used.

THF was freshly distilled from sodium/benzophenone and DMF sequentially dried and stored over 4 Å molecular sieves. Fresh solutions of n-BuLi (1.6 M in hexanes) were used throughout.

Preparative HPLC was performed using Kromasil 60 Å/13 micron silica gel (1 kg).

EXAMPLE 1

5-Tetrazol-5-yl-1H-indole (1a)

A mixture of 5-cyano-1H-indole (88 g), triethylamine hydrochloride (225 g), and sodium azide (150 g) was heated in 1,2-dimethoxyethane (DME) at reflux temperature for 48 hours. The solvent was evaporated in vaciio and the residue was dissolved in ethyl acetate (500 mL) and water (500 mL). pH was adjusted to 10 by addition of concentrated aqueous NaOH solution. The aqueous phase was separated and pH was adjusted to 4 by addition of acetic acid. The precipitated crystalline title compound 1a was filtered off and subsequently dried in vacuo. Yield 82 g, mp 205° C.

EXAMPLE 2

5-(1-Methyltetrazol-5-yl)-1H-indole (2a) and 5-(2-Methyltetrazol-5-yl)-1H-indole (2b)

To a solution of 5-(tetrazol-5-yl)-1H-indole (1a), (95 g) in dry dimethylformamide (DMF) (900 mL) potassium t-butoxide powder (60 g) was added cautiously at 20–25° C. After cooling to 5° C., a solution of iodomethane (145 mL) in DMF was added dropwise. The mixture was allowed to heat slowly to room temperature and was subsequently stirred overnight. The mixture was worked-up according to the general procedure above by extraction with diethyl ether. The resulting mixture of the 1- and 2-methylsubstituted tetrazoles were separated by column chromatography on silica gel (eluted with a 1:1 mixture of heptane and ethyl acetate). Yield 15 g of the title compound 2a, mp 177–180° C. Yield 60 g of the title compound 2b, mp 149–150° C.

EXAMPLE 3

5-(2-Methyltetrazol-5-yl)-3-(1,2,3,6-tetrahydropyridin-4-yl)-1H-indole (3a)

A solution of 5-(2-methyltetrazol-5-yl)-1H-indole (2b) (40 g), piperidin-4-one, hydrate, hydrochloride (80 g) and potassium hydroxide (48 g) in ethanol (1000 mL) was boiled at reflux for 16 hours. After cooling to room temperature, precipitated material was filtered off and carefully washed with water. The remaining crystalline product was dried in

EXAMPLE 4

1-[2-[4-[5-(2-methyltetrazol-5-yl)-1H-indol-3-yl]-1,2,3, 6-tetrahydropyridin-1-yl]ethyl]-2-imidazolidinone (4a)

A mixture of 5-(2-methyltetrazol-5-yl)-3-(1,2,3,6-tetrahydropyridin-4-yl)-1H-indole (3a) (20 g) 1-(2-chloroethyl)imidazolidin-2-one (12.5 g), anhydrous potassium carbonate (12.5 g) and potassium iodide (5 g) was boiled at reflux in methyl isobutyl ketone (MIBK) (600 mL) for 16 hours. The mixture was filtered while still hot. The thus isolated crystalline material was washed with hot methanol (600 mL) followed by washing with water (600 mL). The remaining crystalline title compound 4a was dried in vacuo. Yield 20 g, mp 249–252° C.

EXAMPLE 5

1-[2-[4-[5-(2-Methyltetrazol-5-yl)-1-(4-pyridyl)-1H-indol-3-yl]-1,2,3,6-tetrahydro-1-pyridinyl]ethyl]-2-imidazolidinone (5a)

4-Bromopyridine hydrochloride (4×2g) was added during one hour to a mixture of 1-[2-[4-[5-(2-methyltetrazol-5-yl)-1H-indol-3-yl]-1,2,3,6-tetrahydro-1-pyridinyl]ethyl]-2-imidazolidinone (4a) (5 g), potassium carbonate (9 g), copper powder (1 g), copper iodide (0.3 g), zinc oxide (0.3 g) and N-methyl-2-pyrrolidinone (NMP) (75 mL) at 140–150° C. Heating was continued for additional 4 hours. After cooling, ethyl acetate (500 mL) was added. Inorganic salts were filtered off. Water was added and the organic phase was worked up according to the standard procedure above. The remaining crude product was purified by column chromatography on silica gel, eluted with a 50:50:4 mixture of ethyl acetate, ethanol, and triethylamine. Yield 0.7 g of the title compound 5a. mp 177–178° C. $^1$H NMR (DMSO-$d_6$) δ 2.55–2.65 (m, 4H), 2.75 (t, 2H), 3.20–3.30 (m, 6H) 3.40 (t, 2H), 4.45 (s. 3H), 6.25 (s, 1H), 6.30 (broad t, 1H), 7.75 (dd, 2H, 7.90–8.00 (m, 3H), 8.60 (s, 1H), 8.75 (d, 2H), MS m/z (%): 236 (MH$_2$++), 272 (9%), 245 (17%), 142 (65%), 113 (100%).

EXAMPLE 6

1-[2-[4-[5-(2-Methyltetrazol-5-yl)-1-(4-pyridyl)-1H-indol-3-yl]-1-piperidinyl]ethyl]-2-imidazolidinone (6a)

To a solution of 1-[2-[4-[5-(2-methyl-tetrazol-5-yl)-1H-indol-3-yl]-1,2,3,6-tetrahydro-1-pyridinyl]ethyl]-2-imidazolidinone (4a) (9 g) in glacial acetic acid (180 mL) was added PtO$_2$ and the mixture was hydrogenated in a Parr apparatus at 3 ato overnight. The catalyst was filtered off and acetic acid was removed by evaporation in vacuo. Water (200 mL) and dichloromethane (200 mL) were added. Diluted aqueous ammonia was added to adjust pH to 11. Precipitated crystalline compound was filtered off and dried. Yield 5 g of 1-[2-[4-[5-(2-methyltetrazol-5-yl)-1H-indol-3-yl]-1-piperidinyl]ethyl]-2-imidazolidinone. Further 4 g of the piperidino compound was isolated by work-up of the organic phase. The combined fractions were used without further purification. 4-Bromopyridine hydrochloride (5×3g) was added during one hour to a mixture of the thus isolated 1-[2-[4-[5-(2-methyltetrazol-5-yl)-1H-indol-3-yl]-1-piperidinyl]ethyl]-2-imidazolidinone (9 g), potassium carbonate (20 g), copper powder (2 g), copper iodide (2 g), zinc oxide (0.6 g) and NMP (150 mL) at 140–150° C. Further reaction and work-up as above in Example 5 afforded 0.7 g of the title compound 6a, mp 204–206° C. $^1$H NMR (DMSO-$d_6$): δ 1.70–1.85 (m, 2H), 1.95–2.05 (m, 2H), 2.15 (t 2H), 2.40–2.50 (m, 2H), 2.90 (tt, 1H), 3.00–3.10 (m, 2H), 3.15–3.25 (m, 4H), 3.40–3.50 (m, 2H), 4.45 (s, 3H), 6.20 (s, 1H); 7.20–7.30 (m, 3H), 7.95 (s, 2H), 8.35 (s, 1H), 8.70 (d, 2H). MS m/z (%): 472 (MH+, 6%), 113 (100%).

EXAMPLE 7

1-[2-[4-[5-(Tetrazol-5-yl)-1-(4-fluorophenyl)-1H-indol-3-yl]-1-piperidinyl]ethyl]-2-imidazolidinone hydrochloride (7a)

A suspension of 1-[2-[4-[5-cyano)-1-(4-fluorophenyl)-1H-indol-3-yl]-1-piperi-dinyl]ethyl]-2-imi-dazolidinone (7 g), prepared according to the method in Perregaard et al. *J. Med. Chem.* 1992 (35), 1092–1101, triethylamine hydrochloride (7.5 g) and sodium azide (4.2 g) in DME (100 mL) was heated at reflux for 16 hours. After cooling to room temperature, water (500 mL), triethylamine (5 mL) and ethyl acetate (500 mL) were added. The phases were separated and the organic solvents evaporated in vacuo. The remaining viscous oil was stirred with methanol and solids were filtered off. Methanol was evaporated and the remaining crystalline product was washed successively with acetone and water. The hydrochloride salt of the title compound 7a precipitated from ethanol by adding HCl gas. The crystalline product was stirred with water and finally filtered off and dried. Yield 1.3 g, mp 193–197° C. $^1$H NMR (DMSO-$d_6$): δ 2.20–2.40 (m, 4H), 3.20–3.80 (m, 13H), 6.60 (s, 1H), 7.40 (t, 2H), 7.60–7.70 (m, 4H), 7.95 (d, 1H), 8.75 (s, 1H); MS m/z (%): 475 (MH+, 29), 113 (100%).

EXAMPLE 8

1-(4-Fluorophenyl)-5-tetrazol-5-yl-1H-indole (8a)

A suspension of 5-cyano-1-(4-fluorophenyl)-1H-indole (20 g) (prepared according to the method in Perregaard et al. *J. Med. Chem.* 1992 (35), 1092–1101), triethylamine hydrochloride (35 g) and sodium azide (20 g) in DME (250 mL) was boiled at reflux for 16 hours. Inorganic salts were filtered off and the solvent evaporated in vacuo. The remaining solid material was dissolved in ethyl acetate (500 mL) and water (500 mL) and glacial acetic acid was added. The organic phase was worked-up according to the general procedure above yielding 19 g of crystalline title compound 8a, mp 224–225° C. (washed with diethyl ether).

EXAMPLE 9

1-(4-Fluorophenyl)-5-(2-methyltetrazol-5-yl)-1H-indole (9a)

To a solution of 1-(4-fluorophenyl)-5-tetrazol-5-yl-1H-indole (8a) (19 g) in NMP (200 mL) potassium t-butoxide (8.5 g) was added cautiously at 10° C. followed by dropwise addition of iodomethane (22 g) during 20 minutes. The mixture was allowed to reach room temperature and stirred for another 2 hours. Crude title compound was worked up according to the general procedure above. Purification was performed by column chromatography on silica gel using dichloromethane as eluent. Yield 15 g, mp 131–133° C.

The following derivative was prepared accordingly:

5-(2-ethyltetrazol-5-yl)-1-(4-fluorophenyl)-1H-indole (9b) (oil): $^1$H NMR (CDCl$_3$) δ 1.70 (t, 3H), 4.65 (q, 2 H), 6.75 (d, 1H), 7.20 (t, 2H), 7.30 (d, 1H), 7.40–7.55 (m, 3H), 8.00 (broad d, 1H), 8.50 (broad s, 1H).

EXAMPLE 10

1-(4-Fluorophenyl)-5-hydoxymethyl-1H-indole (10a)

A solution of 5-cyano-1-(4-fluorophenyl)-1H-indole (43.2 g) (prepared as described by Perregaard et al. *J. Med. Chem.* 1992 35, 1092–1101) and potassium hydroxide (43.1 g) in 90% aqueous ethanol (500 mL) was boiled at reflux for 5 days. The solvents were evaporated in vacuo and water (300 mL) was added. The resulting slurry was acidified with concentrated hydrochloric acid. The precipitated 1-(4-fluorophenyl)-1H-indol-5-carboxylic acid (33.5 g) was collected by filtration and dried in vacuo and used without further purification: $^1$H NMR (DMSO-d$_6$) δ 6.85 (d, 1H), 7.45 (t, 2H), 7.55 (d, 1H), 7.65 (dd, 2H), 7.75 (d, 1H), 7.80 (broad d, 1H), 8.10 (broad s, 1H).

A solution of the crude 1-(4-fluorophenyl)-1H-indole-5-carboxylic acid in tetrahydro-furan (700 mL) was added cautiously to a mixture of lithium aluminum hydride (9.8 g) in tetrahydrofuran (400 mL) at 0° C. The resulting mixture was boiled under reflux for 2 h. After cooling to 0° C., water (10 mL), 14% aqueous sodium hydroxide (10 mL) and water (10 mL) was added. Filtration using celite and evaporation of the solvents afforded crystalline title compound 10a (27 g): Mp 69–70° C.; $^1$H NMR (CDCl$_3$) δ 1.85–1.95 (broad s, 1H), 4.75 (s, 2H), 6.65 (d, 1H), 7.15–7.25 (m, 3H), 7.25 (d, 1H), 7.35–7.45 (m, 3H), 7.65 (broad s, 1H).

EXAMPLE 11

1-(4-Fluorophenyl)-5-(2-methyltetrazol-5-ylmethyl)-1H-indole (11a) and 1-(4-Fluorophenyl)-5-(1-methyltetrazol-5-ylmethyl]-1H-indole (11b)

To a solution of 1-(4-fluorophenyl)-5-hydoxymethyl-1H-indole (10a) (21.5 g) and triethyl amine (21.5 mL) in dichloromethane a solution of methanesulfonyl chloride (15.3 g) in dichloromethane was added at 0–5° C. After stirring at 0–5° C. for 2 h, water (600 mL) was added the phases were separated and the aqueous phase was extracted with dichloromethane (500 mL). The combined organic phases were dried (MgSO$_4$) and the solvents evaporated affording 5-chloromethyl-1-(4-fluorophenyl)-1H-indole as an oil (27.5 g). A solution of the crude chloromethyl derivative in dimethyl sulfoxide was added to a solution of sodium cyanide in dimethyl sulfoxide at 80° C. After heating of the reaction mixture at 80° C. for further 40 minutes, the reaction mixture was cooled to room temperature and water (900 ml) was added. The resulting mixture was extracted with diethyl ether (2×1.5 L) and the combined organic phases were washed with brine (2×1.5 L). Drying of the combined organic phases (Na$_2$SO$_4$), evaporation of the solvents and purification by column chromatography on silica gel (ethyl acetate/heptane 1:3) afforded pure 5-cyanomethyl-1-(4-fluorophenyl)-1H-indole as an oil (8.2 g): $^1$H NMR (CDCl$_3$) δ 3.80 (s, 2H), 6.60 (d, 1H), 7.05–7.25 (m, 3H), 7.25 (d, 1H), 7.35–7.45 (m, 3H), 7.60 (broad s, 1H).

A solution of the cyanomethyl compound, sodium azide, triethylamine hydrochloride in 1,2-dimethoxyethane was boiled at reflux for 2 days. After cooling to room temperature, the reaction mixture was filtered and the volatile solvents were evaporated in vacuo. Water (100 mL) and glacial acetic acid (15 mL) were added and the resulting mixture was extracted with ethyl acetate (2×150 mL). The combined organic phases were washed with water (200 mL) and brine (200 mL) and subsequently dried (Na$_2$SO$_4$). Evaporation of the solvents in vacuo gave 1-(4-fluorophenyl)-5-(tetrazol-5-ylmethyl)-1H-indole as an oil containing some residual acetic acid (14 g). A solution of the crude tetrazole in NMP (200 mL) was cooled with ice and potassium tert-butoxide (6.4 g) was added cautiously at 10–20° C. over 20 minutes. When the addition was complete the reaction mixture was cooled at 0° C. and iodomethane (7 mL) was added. After stirring at room temperature for 2 h, water (200 mL) was added and the resulting mixture was extracted with ethyl acetate (2×200 mL). The combined organic phases were washed with water (2×200 mL) and brine (2×250 mL), dried (Na$_2$SO$_4$) and the volatile solvents evaporated in vacuo. The resulting mixture of 1- and 2-methyl-substituted tetrazoles was separated by column chromatography on silica gel (ethyl acetate/heptane 1:2). Evaporation of the fastest eluting fractions in vacuo afforded pure 1-(4-fluorophenyl)-5-(2-methyltetrazol-5-ylmethyl)-1H-indole (11a) as an oil (3.7 g): $^1$H NMR (CDCl$_3$) δ 4.25 (s, 3H), 4.30 (s, 2H), 6.60 (d, 1H), 7.10–7.20 (m, 3H), 7.20 (d, 1H), 7.30–7.45 (m, 3H), 7.60 (broad s,1H).

Evaporation in vacuo of the slowest eluting fractions afforded pure 1-(4-fluorophenyl)-5-(1-methyltetrazol-5-yl) methyl-1H-indole (11b) as an oil (1.5 g): $^1$H NMR (CDCl$_3$) δ 3.80 (s, 3H), 4.35 (s, 2H), 6.50 (d, 1H), 7.00 (broad d, 1H), 7.15 (t, 2H), 7.25 (d, 1H), 7.30–7.40 (m, 3H), 7.45 (broad s, 1H).

EXAMPLE 12

3-(1-t-Butyloxycarbonyl-4-piperidyl)-5-cyano-1-(4-fluorophenyl)-1H-indole (12a)

To a solution of 5-cyano-1-(4-fluorophenyl)-3-(4-piperidyl)-1H-indole (prepared according to the methods in Perregaard et al. *J. Med. Chem.* 1992 (35), 1092–1101) (70 g) and triethylamine (50 mL) in dichloromethane (600 mL) a solution of di-t-butyldicarbonate (45 g) in dichloromethane (200 mL) was added dropwise during 30 minutes at 25° C. After stirring for an additional hour, water (1000 mL) was added and the organic phase was subsequently worked-up according to the general procedure above yielding 64 g of the title compound 12a as a viscous oil, which was used without further purification.

EXAMPLE 13

3-(1-t-Butyloxycarbonyl-4-piperidinyl)-1-(4-fluorophenyl)-5-(2-methyltetrazol-5-yl)-1H-indole (13a)

Following the procedure in Example 8, the cyanoderivative 12a was converted to the corresponding 5-[1-(4-fluorophenyl)-3-(1-t-butyloxycarbonyl-4-piperidinyl)-5-(5-tetra-zolyl)-1H-indole which was methylated according to the procedure in Example 9 to give the title compound 13a.

EXAMPLE 14

1-[2-[4-[1-(4-Fluorophenyl)-5-(2-methyltetrazol-5-yl)-1H-indol-3-yl]piperidin-1-yl]ethyl]-2-imidazolidinone Hydrochloride (14a)

Compound 13a (2.0 g) was dissolved in trifluoroacetic acid (25 mL) and the solution was stirred for 15 minutes. Trifluoroacetic acid was evaporated in vacuo and further excess was flushed off by evaporation twice with MIBK. The remaining viscous oil was dissolved in MIBK (25 mL) and 1-(2-chloroethyl)imidazolidin-2-one (0.9 g), potassium carbonate (1.5 g), and potassium iodide (0.2 g) were added. The mixture was refluxed for 6 hours. Inorganic salts were filtered off and MIBK evaporated. The pure title compound 14a was isolated by column chromatography on silica gel (eluted with a 80:20:4 mixture of ethyl acetate, ethanol and triethylamine). Yield 1.6 g, mp 179–180° C. $^1$H NMR (DMSO-d$_6$) δ 1.70–1.85 (m, 2H), 1.95–2.05 (m, 2H), 2.15–2.30 (m, 2H), 2.90 (tt, 1H), 3.00–3.10 (m, 2H), 3.15–3.35 (m, 6H), 3.40 (t, 2H), 4.40 (s, 3H), 6.25 (broad s, 1H), 7.45 (t, 2H), 7.50 (s, 1H), 7.60–7.70 (m, 3H), 7.90 (d, 1H), 8.40 (s, 1H), MS m/z (%): 489 (MH+, 15%), 461 (28%), 196 (49%), 113 (100%).

EXAMPLE 15

3-[4-[1-(4-Fluorophenyl)-5-(2-methyltetrazol-5-yl)-1H-indol-3-yl]-1,2,3,6-tetrahydropyridin-1-yl]propionitril (15a)

To a solution of 1-(4-fluorophenyl)-5-(2-methyl-5-tetrazolyl)-3-(1,2,3,6-tetrahydro-4-pyridinyl)-1H-indole (21a), (10.2 g) in dichloromethane (100 mL) was added acrylonitril (7.5 g). The mixture was stirred at room temperature for 16 hours. After evaporation of the solvent, the crude title compound 15a remained as a viscous oil which was used without further purification. Yield 12 g.

EXAMPLE 16

1-(4-Fluorophenyl)-5-(2-methyltetrazol-5-yl)-3-[1-[2-(tetrazol-5-yl)ethyl]-1,2,3,6-tetrahydropyridin-4-yl]-1H-indole (16a)

A mixture of 3-[4-[5-(2-methyltetrazol-5-yl)-1-(4-fluorophenyl)-1H-indol-3-yl]-1,2,3,6-tetrahydropyridin-1-yl]propionitril 15a, (3.5 g), sodium azide (2.5 g), and triethylamine hydrochloride (4.5 g) in DME (25 mL) was boiled at reflux for 16 hours. The solvent was evaporated and water (25 mL) and ethyl acetate (1–2 mL) were added after stirring for 0.5 hours the precipitated title compound 16a, was filtered off and dried. Yield 3.2 g, mp 131–132° C.

EXAMPLE 17

1-(4-Fluorophenyl)-5-(2-methyltetrazol-5-yl)-3-[1-[2-(2-methyltetrazo-5-yl)ethyl]-1,2,3,6-tetrahydropyridin-4-yl]-1H-indole (17a) and 1-(4-Fluorophenyl)-5-(2-methyltetrazol-5-yl)-3-[1-[2-(1-methyltetrazol-5-yl)ethyl]-1,2,3,6-tetrahydropyridin-4-yl]-1H-indole, fumarate (17b)

To a solution of 1-(4-fluorophenyl)-5-(2-methyltetrazol-5-yl)-3-[1-[2-tetrazol-5-ylethyl]-1,2,3,6-tetrahydropyridin-4-yl]-1H-indole 16a, (3.8 g) in NMP (30 mL) kept at 10° C. was added potassium t-butoxide (1.4 g). After stirring for 15 minutes, iodomethane (1.8 g) was added still at 10° C. The mixture was allowed to reach room temperature during 1.5 hours. Water (200 mL) and ethyl acetate (100 mL) were added and the organic phase was worked up according to the general procedure above. The crude mixture of the 1- and 2-methylated tetrazoles were purified and separated by column chromatography (eluted with a 90:10:4 mixture of ethyl acetate, ethanol, and triethylamine).

Yield 1.2 g of 1-(4-fluorophenyl)-5-(2-methyltetrazol-5-yl)-3-[1-[2-(2-methyltetrazol-5-yl)ethyl]-1,2,3,6-tetrahydropyridin-4-yl]-1H-indole (17a). Mp 151–152° C. (crystallised from ethyl acetate). $^1$H NMR (CDCl$_3$): δ 2.65 (broad s, 2H), 2.90 (t, 2H), 3.00 (t, 2H), 3.20 (t, 2H), 3.35 (broad s, 2H), 4.35 (s, 3H), 4.40 (s, 3H), 6.35 (broad s, 1H), 7.20–7.30 (m, 3H), 7.40–7.50 (m, 3H), 8.00 (d, 1H), 8.25 (s, 1H); MS m/z: 485 (MH+, 24), 346 (23), 140 (140).

Yield 0.9 g of 1-(4-fluorophenyl)-5-(2-methyltetrazol-5-yl)-3-[1-[2-(1-methyltetrazol-5-yl)-ethyl]-1,2,3,6-tetrahydropyridin-4-yl]-1H-indole, fumarate (17b). Mp 171–173° C. (ethanol). $^1$H NMR (DMSO-d$_6$): δ 2.55–2.65 (m, 4H), 2.80 (t, 2H), 2.90 (t, 2H), 3.15 (t, 2H), 3.30 (broad s, 2H), 4.05 (s, 3H), 4.45 (s, 3H), 6.25 (broad s, 1H), 6.60 (s, 2H), 7.45 (t, 2H), 7.60–7.70 (m, 3H), 7.80 (s, 1H), 7.90 (d, 1H), 8.60 (s, 1H); MS m/z (%): 485 (MH+, 35), 346 (27), 140 (100).

EXAMPLE 18

5-ethynyl-1-(4-Fluorophenyl)-1H-indole (18a)

A mixture of 5-bromo-1-(4-fluorphenyl)-1H-indole (40 g) (prepared as described by Perregaard et al. *J. Med. Chem.* 1992 35, 1092–1101), (trimethylsilyl)acetylen (21.4 g), bis(triphenylphospine)palladium(II) dichloride (2.9 g) copper (I) iodide (1.3 g), triethylamine (40 mL) and acetonitrile (150 mL) was boiled under reflux for 8 hours. After cooling to room temperature, water was added and the resulting mixture was extracted with ethyl acetate (4×300 mL). The combined organic phases were washed with brine (2×800 mL), dried (Na$_2$SO$_4$) and the solvents evaporated in vacuo. A solution of the remaining oil and potassium hydroxide (12.1 g) in a mixture of methanol (500 mL) and water (200 mL) was boiled at reflux for 3 h. The volatile solvents were evaporated in vacuo and a mixture of water (200 mL) and ethyl acetate (1000 mL) was added. The phases were separated and the aqueous phase extracted with ethyl acetate (250 mL). The combined organic phases were dried (Na$_2$SO$_4$) and the volatile solvents evaporated in vacuo. Purification of the remaining oil by column chromatography on silica gel (dichloromethane/heptane 1:6) afforded crystalline pure title compound 18a (11.4 g): Sp 99–100° C.; $^1$H NMR (CDCl$_3$) δ 3.00 (s, 1H), 6.55 (d, 1H), 7.20 (t, 2H), 7.25 (d, 1H), 7.35 (m, 2H), 7.40 (dd, 2H), 7.85 (broad s, 1H).

EXAMPLE 19

1-(4-Fluorophenyl)-5-triazol-4-yl-1H-indole (19a)

A mixture of 5-ethynyl-1-(4-fluorophenyl)-1H-indole (9.6 g) and neat azidotrimethylsilane (21.7 g) was heated in a sealed tube at 170° C. for 24 h. The reaction mixture was cooled to 0° C. and a mixture of dichloromethan (150 mL) and 2 N aqueous sodium hydroxide was added. After stirring at room temperature for 2 h, the mixture was acidified with concentrated hydrochloric acid. The phases were separated and the aqueous phase was extracted with dichloromethane (2×200 mL). The combined organic phases were washed with brine (200 mL), dried (MgSO$_4$) and the volatile solvents evaporated in vacuo affording pure title compound 19a as an oil (11.8 g): $^1$H NMR (CDCl$_3$) δ 6.80 (d, 1H), 7.25 (t, 2H), 7.40 (d, 1H), 7.55 (dd, 2H), 7.60 (d, 1H), 7.75 (broad d, 1H), 8.05 (s, 1H), 8.20 (broad s, 1H).

EXAMPLE 20

1-(4-Fluorophenyl)-5-(2-methyltriazol-4-yl)-1H-indole (20a) and 1-(4-Fluorophenyl)-5-(1-methyltriazol-4-yl)-1H-indole (20b)

A mixture of 1-(4-fluorophenyl)-5-triazol-4-yl-1H-indole (6.0 g), iodomethane (6.7 mL), potassium carbonate (6.0 g) and acetone (100 mL) was boiled under weak reflux for 18 hours. The reaction mixture was filtered and the volatile solvents evaporated in vacuo. The mixture of 1-methyl- and 2-methyl-substituted triazoles was separated by column chromatography on silica gel (ethyl acetate/heptane 1:1). Evaporation of the fastest eluting fractions in vacuo afforded pure 1-(4-fluorophenyl)-5-(2-methyltriazol-4-yl)-1H-indole (20a) as an oil: (2.1 g): $^1$H NMR (CDCl$_3$) δ 4.25 (s, 3H), 6.70 (d, 1H), 7.20 (t, 2H), 7.30 (d, 1H), 7.40–7.55 (m, 3H), 7.65 (broad d, 1H), 7.85 (s, 1H), 8.10 (broad s, 1H). Evaporation of the slowest eluting fractions in vacuo afforded pure 1-(4-fluorophenyl)-5-(1-methyltriazol-4-yl)-1H-indole (20b) as an oil (0.8 g): $^1$H NMR (CDCl$_3$) δ 4.15 (s, 3H), 6.70 (d, 1H), 7.20 (t, 2H), 7.30 (d, 1H), 7.50 (dd, 2H), 7.55 (d, 1H), 7.70 (broad d, 1H), 7.75 (s, 1H), 8.10 (broad s, 1H).

The following compounds were prepared accordingly:
5-(1-ethyltriazol-4-yl)-1-(4-fluorophenyl)-1H-indole (20c):
$^1$H NMR (CDCl$_3$) δ 1.60 (t, 3H), 4.45 (q, 2H), 6.70 (d, 1H), 7.20 (t, 2H), 7.30 (d, 1H), 7.40–7.55 (m, 3H), 7.70 (broad d, 1H), 7.75 (s, 1H), 8.15 (broad s, 1H).

5-(2-ethyltriazol-4-yl)-1-(4-fluorophenyl)-1H-indole (20d) (oil): $^1$H NMR (CDCl$_3$) δ 1.60 (t, 3H), 4.50 (q, 2H), 6.70 (d, 1H), 7.20 (t, 2H), 7.30 (d, 1H), 7.45 (dd, 2H), 7.45 (d, 1H), 7.65 (broad d, 1H), 7.80 (s, 1H), 8.10 (broad s, 1H).

EXAMPLE 21

1-(4-Fluorophenyl)-5-(2-methyl-5-tetrazolyl)-3-(1,2,3,6-tetrahydro-4-pyridinyl)-1H-indole (21a)

A mixture of piperidin-4-one, hydrochloride, hydrate (45 g), glacial acetic acid (250 mL) and trifluoroacetic acid (250 mL) was boiled under reflux. During 30 minutes, 5-(2-methyl-tetrazol-5-yl)-1-(4-fluorophenyl)-1H-indole (9a) (15 g) was added in small portions at a time. The mixture was boiled at reflux for another 1.5 hours. After cooling, the solvents were evaporated. Diethyl ether was added to the remaining semisolid and the resulting crystalline title product was filtered off and dried. Yield 15 g, mp 142–145° C.

The following derivatives were prepared accordingly with the following exception. After evaporation of the volatile solvents, water was added. The aqueous phase was made alkaline by addition of concentrated sodium hydroxide and subsequently extracted with ethyl acetate. The combined organic phases were dried (Na$_2$SO$_4$) and the solvents evaporated in vacuo. The products were crystallised from appropriate solvents if possible.

5-[1-(4-fluorophenyl)-3-(1-methyl-1,2,3,6-tetrahydropyridin-4-yl)-5-(2-methyltetrazol-5-yl-1H-indole (21b): mp 142–144° C. (ethanol); $^1$H NMR (CDCl$_3$) δ 2.45 (s, 3H), 2.60–2.80 (m, 4H), 3.20–3.30 (m, 2H), 4.40 (s, 3H), 6.30–6.40 (m, 1H), 7.20 (t, 2H), 7.25 (s, 1H), 7.40–7.55 (m, 3H), 8.00 (broad d, 1H), 8.75 (s, 1H). MS rnz: 389 (MH+, 5), 318 (60), 346 (99) 289 (37), 263 (100).

5-[1-(4-fluorophenyl)-5-(1-methyltetrazol-5-yl)-3-(1,2,3,6-tetrahydropyridin-4-yl)-1H-indole (21c) (oil): $^1$H NMR (CDCl$_3$) δ 1.85–1.95 (broad s, 1H), 2.50–2.65 (m, 2H), 3.20 (t, 2H), 3.55–3.65 (m. 2H), 4.20 (s, 3H), 6.25–6.35 (m, 1H), 7.25 (t, 2H), 7.35 (s, 1H), 7.50 (dd, 2H), 7.50 (m, 2H), 8.30 (broad s, 1H).

5-[5-(2-ethyltetrazol-5-yl)-1-(4-fluorophenyl)-3-(1,2,3,6-tetrahydropyridin-4-yl)-1H-indole (21i) (oil): $^1$H NMR (CDCl$_3$) δ 1.65 (t, 3H), 2.05–2.25 (broad s, 1H), 2.40–2.60 (m, 2H), 3.15 (t, 2H), 3.55–3.70 (m, 2H), 4.65 (q, 2H), 6.35–6.50 (m, 1H), 7.10–7.25 (m, 3H), 7.35–7.50 (m, 3H), 8.00 (broad d, 1H), 8.75 (broad s, 1H).

1-(4-fluorophenyl)-5-[(1-methyltetrazol-5-yl)methyl]-3-(1,2,3,6-tetrahydropyridin-4-yl)-1H-indole (21d) (oil): $^1$H NMR (CDCl$_3$) δ1.80–1.95 (broad s, 1H), 2.40–2.55 (m, 2H), 3.15 (t, 2H), 3.55–3.65 (m, 2H), 3.80 (s, 3H), 4.40 (s, 2H), 6.15–6.25 (m, 1H), 7.00 (broad d, 1H), 7.20 (t, 2H), 7.25 (d, 1H), 7.30–7.45 (m, 3H), 7.75 (broad s, 1H).

1-(4-fluorophenyl)-5-[(2-methyltetrazol-5-yl)methyl]-3-(1,2,3,6-tetrahydropyridin-4-yl)-1H-indole (21e) (oil): $^1$H NMR (CDCl$_3$) δ 2.05–2.20 (broad s, 1H), 2.45–2.55 (m, 2H), 3.15 (t, 2H), 3.55–3.65 (m, 2H), 4.25 (s, 3H), 4.35 (s, 2H), 6.25–6.30 (m, 1H), 7.10–7.25 (m, 4H), 7.30–7.45 (m, 3H), 7.90 (broad s, 1H).

1-(4-fluorophenyl)-5-(1-methyltriazol-4-yl)-3-(1,2,3,6-tetrahydropyridin-4-yl)-1H-indole (21f) (oil): $^1$H NMR (CDCl$_3$) δ 2.50–2.60 (m, 2H), 2.60–2.70 (broad s, 1H), 3.15 (t, 2H), 3.60–3.70 (m, 2H), 4.15 (s, 3H), 6.30–6.40 (m, 1H), 7.15–7.25 (m, 3H), 7.35–7.50 (m, 3H), 7.65 (broad d, 1H), 7.75 (s, 1H), 8.40 (broad s, 1H).

1-(4-fluorophenyl)-5-(2-methyltriazol-4-yl)-3-(1,2,3,6-tetrahydropyridin-4-yl)-1H-indole (21g) (oil): $^1$H NMR (CDCl$_3$) δ 2.05–2.25 (broad s, 1H), 2.45–2.60 (m, 2H), 3.15 (t, 2H), 3.60–3.70 (m, 2H), 4.25 (s, 3H), 6.30–6.40 (m, 1H), 7.20 (t, 2H), 7.25 (s, 1H), 7.40–7.50 (m, 3H), 7.65 (broad d, 1H), 7.85 (s, 1H), 8.35 (broad s, 1H).

5-(2-ethyltriazol-4-yl)-1-(4-fluorophenyl)-3-(1,2,3,6-tetrahydropyridin-4-yl)-1H-indole (21h) (oil): $^1$H NMR (CDCl$_3$) δ 1.60 (t, 3H), 1.85–2.00 (broad s, 1H), 2.45–2.60 (m, 2H), 3.15 (t, 2H), 3.60–3.70 (m, 2H), 4.50 (q, 2H), 6.30–6.40 (m, 1H), 7.20 (t, 2H), 7.25 (s, 1H), 7.40–7.50 (m, 3H), 7.65 (broad d, 1H), 7.85 (s, 1H), 8.30 (broad s, 1H).

EXAMPLE 22

1-[2-[4-[1-(4-Fluorophenyl)-5-(2-methyltetrazol-5-yl)-1H-indol-3-yl]-1,2,3,6-tetrahydropyridin-1-yl]ethyl]-2-imidazolidinone (22a)

A mixture of 1-(4-fluorophenyl)-5-(2-methyl-5-tetrazolyl)-3-(1,2,3,6-tetrahydro-4-pyridinyl)-1H-indole (21a) (4 g), 1-(2-chloroethyl)imidazolidin-2-one (1.8 g), potassium carbonate (2.1 g) and potassium iodide (0.5 g) in MIBK (80 mL) was boiled at reflux for 20 hours. After cooling, inorganic salts were filtered off and the solvent evaporated in vacuo. The title compound crystallised from ethyl acetate. Yield 3.0 g. Mp 201–203° C. $^1$H NMR (CDCl$_3$): δ 2.60–2.70 (m, 4H), 2.80 (t, 2H), 3.30 (broad s, 2H), 3.35–3.45 (m, 4H), 3.55 (t, 2H), 4.40 (s, 3H), 4.65 (s, 1H), 6.35 (broad s, 1H), 7.20 (t, 2H), 7.25 (s, 1H), 7.40–7.50 (m, 3H), 7.95 (d, 1H), 8.25 (s, 1H); MS m/z (%): 487 (MH+, 12), 142 (49), 113 (100).

The following derivatives were prepared accordingly:

1-[2-[4-[1-(4-fluorophenyl)-5-(1-methyltetrazol-5-yl)-1H-indol-3-yl]-1,2,3,6-tetrahydropyridin-1-yl]ethyl]-2-imidazolidinone (22b): Mp 198–200° C. (acetone). $^1$H NMR (CDCl$_3$) δ 2.55–2.75 (m, 4H), 2.80 (t, 2H), 3.25–3.35 (m, 2H), 3.35–3.50 (m, 4H), 3.50–3.60 (m, 2H), 4.20 (s, 3H), 4.55 (broad s, 1H), 6.20–6.30 (m, 1H), 7.25 (t, 2H), 7.35 (s, 1H), 7.50 (dd, 2H), 7.50–7.60 (m, 2H), 8.35 (broad s, 1H); MS m/z: 487 (MH+, 8), 346 (7), 142 (100), 113 (95).

1-[2-[4-[5-(2-ethyltetrazol-5-yl-1-(4-fluorophenyl)-1H-indol-3-yl]-1,2,3,6-tetrahydropyridin-1-yl]ethyl]-2-imidazolidinone (22c): Mp 179–181° C. (diethyl ether). $^1$H NMR (CDCl$_3$) δ 1.70 (t, 3H), 2.60–2.75 (m, 4H), 2.80 (t, 2H), 3.25–3.35 (m, 2H), 3.35–3.50 (m, 4H), 3.50–3.60 (m, 2H), 4.45 (broad s, 1H), 4.70 (q, 2H), 6.30–6.40 (m, 1H), 7.20 (t, 2H), 7.25 (s, 1H), 7.50–7.60 (m, 3H), 8.00 (broad d, 1H), 8.75 (broad s, 1H); MS m/z: 501 (MH+, 6), 142 (96), 113 (100).

1-[2-[4-[1-(4-fluorophenyl)-5-[(1-methyltetrazol-5-yl)methyl]-1H-indol-3-yl]-1,2,3,6-tetrahydropyridin-1-yl]ethyl]-2-imidazolidinone (22d): Mp 174–176° C. (ethanol). $^1$H NMR (CDCl$_3$) δ 2.55–2.65 (m, 4H), 2.80 (t, 2H), 3.20–3.35 (m, 2H), 3.35–3.50 (m, 4H), 3.50–3.65 (m, 2H), 3.80 (s, 3H), 4.35 (broad s, 1H), 4.40 (s, 2H), 6.10–6.20 (m, 1H), 7.05 (broad d, 1H), 7.15–7.30 (m, 3H), 7.30–7.45 (m, 3H), 7.75 (broad s, 1H); MS m/z: 501 (MH+, 6), 142 (100), 113 (97)

1-[2-[4-[1-(4-fluorophenyl)-5-[(2-methyltetrazol-5-yl)methyl]-1H-indol-3-yl]-1,2,3,6-tetrahydropyridin-1-yl]ethyl]-2-imidazolidinone (22e): Mp 129–131° C. (ethanol). $^1$H NMR (CDCl$_3$) δ 2.55–2.75 (m, 4H), 2.80 (t, 2H), 3.25–3.35 (m, 2H), 3.35–3.50 (m, 4H), 3.50–3.65 m, 2H), 4.30 (s, 3H), 4.35 (s, 2H), 4.50 (broad s, 1H), 6.20–6.25 (m, 1H), 7.10–7.25 (m, 4H), 7.30–7.45 (m, 3H), 7.90 (broad s, 1H); MS m/z: 501 (MH+, 22), 142 (100), 113 (91).

1-[2-[4-[1-(4-fluorophenyl)-5-(1-methyltriazol-4-yl)-1H-indol-3-yl]-1,2,3,6-yl]ethyl]-2-imidazolidinone (22f) (oil): $^1$H NMR (CDCl$_3$) δ 2.60–2.75 (m, 4H), 2.80 (t, 2H), 3.25–3.35 (m, 2H), 3.35–3.50 (m, 4H), 3.50–3.60 (m, 2H), 4.15 (s, 3H), 4.70 (broad s, 1H), 6.25–6.35 (broad s, 1H), 7.20 (t, 2H), 7.25 (s, 1H), 7.40–7.50 (m, 3H), 7.70 (broad d, 1H), 7.80 (s , 1H), 8.40 (broad s, 1H).

1-[2-[4-[1-(4-fluorophenyl)-5-(2-methyltriazol-4-yl)-1H-indol-3-yl]-1,2,3,6-tetrahydropyridin-1-yl]ethyl]-2-imidazolidinone (22g): Mp 175–177° C. (diethyl ether). $^1$H NMR (CDCl$_3$) δ 2.55–2.75 (m, 4H), 2.80 (t, 2H), 3.25–3.35 (m, 2H), 3.35–3.50 (m, 4H), 3.50–3.60 (m, 2H), 4.25 (s, 3H), 4.85 (broad s, 1H), 6.25–6.35 (broad s, 1H), 7.20 (t, 2H), 7.25 (s, 1H), 7.40–7.55 (m, 3H), 7.65 (broad d, 1H), 7.85 (s, 1H), 8.30 (broad s, 1H).; MS m/z: 486 (MH+), 142 (83), 113 (100).

1-[2-[4-[5-(1-ethyltriazol-4-yl)-1-(4-fluorophenyl)-1H-indol-3-yl]-1,2,3,6-tetrahydropyridin-1-yl]ethyl]-2-imidazolidinone (22h) (oil): $^1$H NMR (CDCl$_3$) δ 1.65 (t, 3H), 2.60–2.75 (m, 4H), 2.75 (t, 2H), 3.25–3.35 (m, 2H), 3.35–3.50 (m, 4H), 3.50–3.60 (m, 2H), 4.50 (q, 2H), 4.70 (broad s, 1H), 6.30–6.40 (broad s, 1H), 7.15–7.30 (m, 3H), 7.40–7.50 (m, 3H), 7.70 (broad d, 1H), 7.80 (s , 1H), 8.40 (broad s, 1H).

1-[2-[4-[5-(2-ethyltriazol-4-yl)-1-(4-fluorophenyl)-1H-indol-3-yl]-1,2,3,6-tetrahydropyridin-1-yl]ethyl]-2-imidazolidinone (22i): Mp 143–145° C. (diethyl ether). $^1$H NMR (CDCl$_3$) δ 1.60 (t, 3H), 2.60–2.75 (m, 4H), 2.80 (t, 2H), 3.30–3.35 (m, 2H), 3.35–3.50 (m, 4H), 3.50–3.60 (m, 2H), 4.50 (q, 2H), 4.85 (broad s, 1H), 6.25–6.35 (broad s, 1H), 7.15–7.30 (m, 3H), 7.40–7.50 m, 3H), 7.65 (broad d, 1H), 7.85 (s, 1H), 8.30 (broad s, 1H); MS m/z: 500 (MH+), 142 (86), 113 (100).

EXAMPLE 23

The following derivatives were prepared according to the procedure described for the preparation of 1-[2-[4-[5-(2-methyl-tetrazol-5-yl)-1H-indol-3-yl]-1-piperidinyl]ethyl]-2-imidazolidinone (6a) from1-[2-[4-[5-(2-methyltetrazol-5-yl)-1H-indol-3-yl]-1,2,3,6-tetrahydro-1-pyridinyl]ethyl]-2-imidazolidinone (4a) in Example 6:

1-[2-[4-[5-(2-ethyltetrazol-5-yl)-1-(4-fluorophenyl)-1H-indol-3-yl]-1-piperidinyl]ethyl]-2-imidazolidinone dihydrochloride (23a): Mp 172–174° C. (diethyl ether). $^1$H NMR (CDCl$_3$) δ 2.75 (t, 3H), 2.15–2.35 (m, 4H), 2.45–2.75 (m, 2H), 2.85–3.00 (m, 2H), 3.05–3.20 (m, 1H), 3.35–3.80 (m. 8H), 4.60 broad s, 1H), 4.75 (q, 2H), 7.15–7.35 (m, 3H), 7.50 (dd, 2H), 7.55 (d, 1H), 8.05 (broad d, 1H), 8.50 (broad s, 1H); MS m/z: 503 (MH+, 21), 475 (34), 432 (10), 196 (38), 113 (100).

1-(4-fluorophenyl)-3-(1-methyl-4-piperidinyl)-5-(2-methyltetrazol-5-yl)-1H-indole (23b): Mp 148–150° C. (acetone). $^1$H NMR (CDCl$_3$) δ 1.75–2.00 (m, 2H); 2.10–2.25 (m, 4H)2.35 (s, 3H), 2.95 (tt, 1H), 2.95–3.10 (m, 2H), 4.40 (s, 3H), 7.10 (s, 1H), 7.20 (t, 2H), 7.45 (dd, 2H), 7.50 (d, 1H), 8.00 (broad d, 1H), 8.50 (broad s, 1H); MS m/z: 391 (MH+, 12), 363 (13), 334 (17), 308 (13), 98 (100), 70 (77).

1-[2-[4-[(-(4-fluorophenyl)-5-[(1-methyltetrazol-5-yl) methyl]-1H-indol-3-yl]-1-piperidinyl]ethyl]-2-imidazolidinone 2.5 fumarate (23c): Mp 169–171° C. (ethanol). $^1$H NMR (DMSO-d$_6$) δ 1.75–2.00 (m, 2H), 2.00–2.15 (m, 2H), 2.55–2.75 (m, 2H), 2.85 (t, 2H), 2.95 (tt, 1H), 3.20–3.50 (m, 8H), 4.00 (s, 3H), 4.40 (s, 2H), 6.40 (broad s, 1H), 6.60 (s, 5H), 7.05 (broad d, 1H), 7.30–7.50 (m, 4H), 7.50 (dd, 2H), 7.65 (broad s, 1H); MS m/z: 503 (MH+, 100), 446 (7), 419 (10), 194 (36), 168 (32), 113 (65).

1-[2-[4-[1-(4-fluorophenyl)-5-[(2-methyltetrazol-5-yl) methyl]-1H-indol-3-yl]-1-piperidinyl]ethyl]-2-imazolidinone 2.25 fumarate (23d): Mp 171–173° C. (methanol). $^1$H NMR (DMSO-d$_6$) δ 1.75–1.95 (m, 2H), 1.95–2.15 (m, 2H), 2.45–2.60 (m, 2H), 2.70–2.85 (m, 2H), 5 2.95 (tt, 1H), 3.15–3.35 (m, 6H), 3.35–3.50 (m, 2H), 4.30 (broad s, 5H), 6.35 (broad s, 1H), 6.60 (s, 4.5H), 7.10 (broad d, 1H), 7.35–7.45 (m, 4H), 7.60 (dd, 2H), 7.70 (broad s, 1H); m/z: 503 (MH+, 11), 419 (10), 194 (82), 168 (69), 113 (100).

1-[2-[4-[1-(4-fluorophenyl)-5-(1-methyltriazol-4-yl)-1H-indol-3-yl]-1-piperidinil]ethyl]-2-imidazolidinone (23e): Mp 116–118° C. (diethyl ether). $^1$H NMR (CDCl$_3$) δ 1.70–1.90 (m, 2H), 2.05–2.30 (m, 4H), 2.60 (t, 2H), 2.95 (tt, 1H), 3.00–3.15 (m, 2H), 3.30–3.45 (m, 4H), 3.50–3.60 (m, 2H), 4.15 (s, 3H), 4.40 (broad s, 1H), 7.05 (s, 1H), 7.20 (t, 2H), 7.45 (dd, 2H), 7.50 (d, 1H), 7.60 (broad d, 1H), 7.75 (s, 1H), 8.20 (broad s, 1H); MS m/z: 488 (MH+, 29), 194 (28), 168 (23), 113 (100).

1-[2-[4-[1-(4-fluorophenyl)-5-(2-methyltriazol-4-yl)-1H-indol-3-yl]-1-piperidinyl]ethyl]-2-imidazolidinone (23f): Mp 203–204° C. (ethanol). $^1$H NMR (CDCl$_3$) δ 1.70–1.90 (m, 2H), 2.05–2.15 (m, 2H), 2.20–2.30 (m, 2H), 2.60 (t, 2H), 2.90 (tt, 1H), 3.05–3.15 (m, 2H), 3.35–3.50 (m, 4H), 3.50–3.60 (m, 2H), 4.25 (s, 3H), 4.40 (broad s, 1H), 7.05 (s, 1H), 7.20 (t, 2H), 7.45 (dd, 2H), 7.50 (d, 1H), 7.60 (broad d, 1H), 7.85 (s, 1H), 8.05 (broad s, 1H); MS m/z: 488 (MH+, 49), 196 (35), 113 (100).

1-[2-[4-[5-(1-ethyltriazol-4-yl)-1-(4-fluorophenyl)-1H-indol-3-yl]-1-piperidinyl]ethyl]-2-imidazolidinone (23g): Mp 132–134° C. (ethanol). $^1$H NMR (CDCl$_3$) δ 1.60 (t, 3H), 1.70–1.95 (m, 2H), 2.05–2.30 (m, 4H), 2.55 (t, 2H), 2.90 (tt, 1H), 3.00–3.15 (m, 2H), 3.30–3.45 (m, 4H), 3.45–3.60 (m, 2H), 4.30 (broad s, 1H), 4.45 (q, 2H), 7.05 (s, 1H), 7.10 (t, 2H), 7.35–7.50 (m, 3H), 7.60 (broad d, 1H), 7.75 (s, 1H), 8.15 (broad s, 1H); MS m/z: 502 (MH+, 100), 113 (86).

1-[2-[4-[5-(2-ethyltriazol-4-yl)-1-(4-fluorophenyl)-1H-indol-3-yl]-1-piperidinyl]ethyl]-2-imidazolidinone (23h): Mp 173–175° C. (ethyl acetate). $^1$H NMR (CDCl$_3$) δ 1.60 (t, 3H), 1.75–1.95 (m, 2H), 2.05–2.15 (m, 2H), 2.20–2.35 (m, 2H), 2.60 (t, 2H), 2.95 (tt, 1H), 3.05–3.15 (m, 2H), 3.35–3.50 (m, 4H), 3.50–3.60 (m, 2H), 4.30 (broad s, 1H), 4.55 (q, 2H), 7.10 (s, 1H), 7.20 (t, 2H), 7.35–7.50 (m, 3H), 7.60 (broad d, 1H), 7.85 (s, 1H), 8.05 (broad s, 1H); MS m/z: 502 (MH+, 47), 196 (28), 113 (100).

1-[2-[4-[1-(4-Fluorophenyl)-5-(pyrimidine-2-yl)-1H-indol-3-yl]-1-piperidinyl]ethyl]-2-imidazolidinone (23i)

1-[2-[4-[1-(4-Fluorophenyl)-5-(pyridine-2-yl)-1H-indol-3-yl]-1-piperidinyl]ethyl]-2-imidazolidinone (23j)

1-[2-[4-[1-(4-Fluorophenyl)-5-(pyridine-3-yl)-1H-indol-3-yl]-1-piperidinyl]ethyl]-2-imidazolidinone (23k)

1-[2-[4-[1-(4-Fluorophenyl)-5-(pyridine-4-yl)-1H-indol-3-yl]-1-piperidinyl]ethyl]-2-imidazolidinone (23l)

1-[2-[4-[1-(4-Fluorophenyl)-5-(1-methyl-1H-pyrazol-3-yl)-1H-indol-3-yl]-1-piperidinyl]ethyl]-2-imidazolidinone (23m)

1-[2-[4-[1-(4-Fluorophenyl)-5-(1-methyl-1H-pyrazol-4-yl)-1H-indol-3-yl]-1-piperidinyl]ethyl]-2-imidazolidinone (23n)

1-[2-[4-[1-(4-Fluorophenyl)-5-(1-methyl-1H-pyrazol-5-yl)-1H-indol-3-yl]-1-piperidinyl]ethyl]-2-imidazolidinone (23o)

1-[2-[4-[1-(4-Fluorophenyl)-5-(1-methyl-1H-pyrazol-2-yl)-1H-indol-3-yl]-1-piperidinyl]ethyl]-2-imidazolidinone (23p)

1-[2-[4-[1-(4-Fluorophenyl)-5-(1-methyl-1H-1,2,4-triazole-3-yl)-1H-indol-3-yl]-1-piperidinyl]ethyl]-2-imidazolidinone (23q)

1-[2-[4-[1-(4-Fluorophenyl)-5-(pyrimidine-5-yl)-1H-indol-3-yl]-1-piperidinyl]ethyl]-2-imidazolidinone (23r)

EXAMPLE 24

1-(4-Fluorophenyl)-5-(pyrimidine-2-yl)-1H-indole (24a)

1-(4-Fluorophenyl)-5-bromo-1H-indole (5 g, 17.2 mmol) in THF (10 mL) was added during 3 minutes to a solution of n-BuLi (1.6 M, 26 mmol) in THF (100 mL) at −78° C. The solution was stirred for 4 minutes at −78° C. before addition of ZnCl$_2$ (1.0 M in THF, 32 mmol) and further 30 minutes at −78° C. 2-Bromopyrimidine (5 g, 31 mmol), Pd(PPh$_3$)$_4$ (3 mol %, 0.6 g) and DMF (75 mL) was added and the solution was slowly heated to 80° C. and stirred at this temperature for 4 h. After cooling to rt water was added and the solution was extracted with ethyl acetate. The combined organic phases were washed with water and CaCl$_2$ (sat.), dried (MgSO$_4$) and the solvents evaporated in vacou. The crude product was purified by preparative HPLC (THF/MeOH/heptane 20/10/70); Yield: 2.5 g, MS m/z (%): 290 (MH$^+$, 37), Mp 185–187° C. (toluene). $^1$H-NMR (CDCl$_3$) δ 6.78 (d, 1H), 7.13 (t, 1H), 7.20–7.29 (m, 3H), 7.31 (d, 1H), 7.45–7.56 (m, 3H), 8.35 (d, 2H), 8.79 (d, 2H), 8.83 (s, 1H).

The following derivatives were prepared accordingly:

1-(4-Fluorophenyl)-5-(pyridine-2-yl)-1H-indole (24b)

$^1$H-NMR (CDCl$_3$) δ 6.75 (d, 1H), 7.19 (dd, 1H), 7.23 (t, 2H), 7.31 (d, 1H), 7.49 (m, 2H), 7.53 (d, 1H), 7.4 (td, 1H), 7.91 (dd, 1H), 8.30 (d, 1H) 8.70 (d, 1H) MS m/z (%): 289 (MH$^+$, 59), Mp 119–121° C. (toluene).

1-(4-Fluorophenyl)-5-(pyridine-3-yl)-1H-indole (24c)

$^1$H-NMR (CDCL$_3$) δ 6.74 (d, 1H), 7.17–7.28 (m, 2H), 7.30–7.40 (m, 2H), 7.43 (dd, 1H), 7.45–7.50 (m, 2H), 7.53 (d, 1H), 7.88 (d, 1H), 7.92 (d, 1H), 8.56 (dd, 1H), 8.91 (d, 1H) MS m/z (%): 289 (MH$^+$, 42), Mp 108–110° C. (toluene).

1-(4-Fluorophenyl)-5-(1-methyl-1H-pyrazol-5-yl)-1H-indole (24d)

$^1$H-NMR (CDCl$_3$) δ 3.91 (s, 3H), 6.31 (d, 1H), 6.73 (d, 1H), 7.2–7.3 (m, 3H), 7.34 (d, 1H), 7.40–7.60 (m, 4H), 7.71 (s, 1H) MS m/z (%): 292 (MH$^+$, 10), Mp 135–137° C. (toluene).

1-(4-Fluorophenyl)-5-(1-methyl-1H-pyrazol-4-yl)-1H-indole (24e)

$^1$H-NMR (CDCL$_3$) δ 3.94 (s, 3H), 6.66 (s, 1H) 7.10–7.25 (m, 3H), 7.33 (s, 1H), 7.40–7.50 (m, 3H), 7.60 (s, 1H), 7.70–7.80 (m, 2H) MS m/z (%): 292 (MH$^+$, 8%). Mp 144–145° C. (toluene).

1-(4-Fluorophenyl)-5-(1-methyl-1H-pyrazol-3-yl)-1H-indole (24f)

$^1$H-NMR (CDCl$_3$) δ 3.95 (s, 3H), 6.56 (d, 1H), 6.68 (d, 1H), 7.1–7.3 (m, 3H), 7.36 (d, 1H), 7.4–7.5 (m, 3H), 7.70 (dd, 1H), 8.09 (s, 1H); MS m/z (%): 292 (MH$^+$, 30), Mp 123–125° C. (toluene).

1-(4-Fluorophenyl)-5-(1-methyl-1H-imidazole-2-yl)-1H-indole (24g)

$^1$H-NMR (CDCl$_3$) δ 3.43 (s, 3H), 6.65 (d, 1H), 6.71 (s, 1H), 7.20–7.30 (m, 4H), 7.33 (d, 1H), 7.37 (d, 1H), 7.40 (m, 2H), 7.49 (s, 1H); MS m/z (%): 292 (MH$^+$, 25).

1-(4-Fluorophenyl)-5-(1-methyl-1H-1,2,4-triazole-3-yl)-1H-indole (24h)

$^1$H-NMR (CDCl$_3$) δ 3.96 (s, 3H), 6.73 (d, 1H), 7.10–7.26 (m, 2H), 7.29 (d, 1H), 7.40–7.60 (m, 3H), 7.98 (d, 1H), 8.05 (s, 1H), 8.44 (s, 1H); MS m/z (%): 293 (MH$^+$, 16).

1-(4-Fluorophenyl)-5-(pyrimidine-5-yl)-1H-indole (24i)

$^1$H-NMR (CDCl$_3$) δ 6.77 (d, J=3.0 Hz, 1H), 7.20–7.30 (m, 2H), 7.22 (d, J=3.5 Hz, 1H), 7.42 (dd, J=8.5 Hz, 1H), 7.45–7.49 (m, 2H), 7.57 (d, J=8.5 Hz, 1H), 7.89 (s, 1H), 9.01 (s, 2H) 9.18 (s, 1H) MS m/z (%): 290 (MH$^+$, 18).

1-(4-Fluorophenyl)-5-(pyridine-4-yl)-1H-indole (24j)

EXAMPLE 25

1-(4-Fluorophenyl)-5-(trimethylstannyl)-1H-indole (25a)

1-(4-Fluorophenyl)-5-bromo-1H-indole (5 g, 17.2 mmol) in THF (20 mL) was added during 3 minutes to a solution of n-BuLi (1.6 M, 26 mmol) in THF (200 mL) at −78° C. The solution was stirred for 4 minutes at −78° C. before addition of trimethylstannyl chloride (10 g, 50 mmol) in THF (10 mL). The reaction mixture was allowed to warm up to room temperature and stirred for 1 h. After evaporation of the solvent the crude product was purified by flash chromatography (EtOAc/Heptane 5/100). Yield: 3.6 g. Mp 61–63° C. (EtOAc/Heptane).

$^1$H-NMR (CDCl$_3$) δ 0.32 (s+d+d, 9H), 6.50 (d, 1H), 7.10–7.35 (m, 4H) 7.40–7.50 (m, 3H), 7.82 (s+d+d, 1H)

EXAMPLE 26

1-(4-Fluorophenyl)-5-(1-methyl-1H-pyrazol-3-yl)-1H-indole (26a)

1-(4-Fluorophenyl)-5-(trimethylstannyl)-1H-indole (1 g, 2.7 mmol), Pd(PPh$_3$)$_4$ (62 mg, 0.05 mmol) and 3-iodo-1-methylpyrazole (0.6 g, 2.9 mmol) was dissolved in dry DMF (30 mL) and stirred at 100° C. for 2 h. The reaction was quenched with water and extracted with ethyl acetate. The combined organic phases were washed with saturated CaCl$_2$, dried (MgSO$_4$), filtered and the solvent was evaporated in vacou. The product was purified by flash chromatography (THF/Heptane/MeOH 20/70/10); Yield 400 mg. $^1$H-NMR as above.

The following derivative was prepared accordingly 1-(4-Fluorophenyl)-5-(1-methyl-1H-pyrazol-4-yl)-1H-indole (26b)

Yield 360 mg. $^1$H-NMR as above.

EXAMPLE 27

1-[2-[4-[1-(4-Fluorophenyl)-5-(1,2,3-triazole-4-yl)-1H-indol-3-yl]-1,2,3,6-tretrahydropyridin-1-yl]ethyl]-2-imidazolidinone (27a)

1-[2-(1,5-dioxa-9-aza-spiro[5,5]undecane-9-yl)-ethyl]-imidazolidin-2-on (17 g, 63 mmol (prepared by alkylation of 1,5-dioxa-9-aza-spiro[5.5]undecane by methods obvious to the synthetic chemist) was dissolved in acetic acid (30 mL) and trifluoroacetic acid (12 mL) and added during 0.5 h to a refluxing solution of 1-(4-fluorophenyl)-5-(1,2,3-triazol-4-yl)-1H-indole (5.8 g, 21 mmol) in acetic acid (30 mL) and trifluoroacetic acid (12 mL). After refluxing for further 50 min, the solution was cooled to room temperature, and the solvent evaporated in vacuo. Water was added, and pH was adjusted to 4–5 using NaOH. The aqueous phase was extracted with ethyl acetate, washed with brine and dried (MgSO$_4$). The product was purified by flash chromatography (EtOAc/EtOH/TEA 50/46/4). Yield: 2.0 g.

$^1$H-NMR δ 2.55–2.68 (m, 4H), 2.70–2.80 (t, 2H), 3.17–3.35 (m, 6H), 3.40–3.60 (m, 3H), 6.25 (s, 1H), 6.35 (broad s, 1H), 7.45 (t, 3H), 7.68 (d, 1H), 7.70 (d, 1H), 7.72 (s, 1H), 7.78 (d, 1H), 8.37 (s, 1H), 8.40 (s, 1H).

1-[2-[4-[1-(4-Fluorophenyl)-5-(pyrimidine-2-yl)-1H-indol-3-yl]-1,2,3,6-tetrahydropyridin-1-yl]ethyl]-2-imidazolidinone (27b)

1-[2-[4-[1-(4-Fluorophenyl)-5-(pyridine-2-yl)-1H-indol-3-yl]-1,2,3,6-tetrahydropyridin-1-yl]ethyl]-2-imidazolidinone (27c)

1-[2-[4-[1-(4-Fluorophenyl)-5-(pyridine-3-yl)-1H-indol-3-yl]-1,2,3,6-tetrahydropyridin-1-yl]ethyl]-2-imidazolidinone (27d)

1-[2-[4-[1-(4-Fluorophenyl)-5-(pyridine-4-yl)-1H-indol-3-yl]-1,2,3,6-tetrahydropyridin-1-yl]ethyl]-2-imidazolidinone (27e)

1-[2-[4-[1-(4-Fluorophenyl)-5-(1-methyl-1H-pyrazol-3-yl)-1H-indol-3-yl]-1,2,3,6-tetrahydropyridin-1-yl]ethyl]-2-imidazolidinone (27f)

1-[2-[4-[1-(4-Fluorophenyl)-5-(1-methyl-1H-pyrazol-4-yl)-1H-indol-3-yl]-1,2,3,6-tetrahydropyridin-1-yl]ethyl]-2-imidazolidinone (27g)

1-[2-[4-[1-(4-Fluorophenyl)-5-(1-methyl-1H-pyrazol-5-yl)-1H-indol-3-yl]-1,2,3,6-tetrahydropyridin-1-yl]ethyl]-2-imidazolidinone (27h)

1-[2-[4-[1-(4-Fluorophenyl)-5-(1-methyl-1H-pyrazol-2-yl)-1H-indol-3-yl]-1,2,3,6-tetrahydropyridin-1-yl]ethyl]-2-imidazolidinone (27i)

1-[2-[4-[1-(4-Fluorophenyl)-5-(1-methyl-1,2,4-triazole-3-yl)-1H-indol-3-yl]-1,2,3,6-tetrahydropyridin-1-yl]ethyl]-2-imidazolidinone (27j)

1-[2-[4-[1-(4-Fluorophenyl)-5-(pyrimidine-5-yl)-1H-indol-3-yl]-1,2,3,6-tetrahydropyridin-1-yl]ethyl]-2-imidazolidinone (27k)

EXAMPLE 28

1-[2-[4-[1-(4-Fluorophenyl)-5-(1,2,3-triazole-4-yl)-1H-indol-3-yl]-1-piperidinyl]-2-imidazolidinone (28a)

1-[2-[4-[1-(4-fluorophenyl)-5-(1,2,3-triazole-4-yl)-1H-indol-3-yl]-1,2,3,6-tetrahydropyridin-1-yl]ethyl]-2-imidazolidinone (2 g) in acetic acid (50 mL) was hydrogenated, using PtO$_2$ (200 mg) as catalyst, for 14 h.

After filtration of the reaction mixture the solvent was evaporated. The product was finally purified by preparative HPLC-MS and freeze dried. Yield 300 mg (trifluoro acetate). Mass: (MH$^+$=474) (free base).

$^1$H-NMR δ 1.95–2.15 (m, 4H), 2.15–2.25 (m, 2H), 2.30 (d, 2H), 3.15–3.25 (m, 1H), 3.25–3.35 (m, 2H), 3.35–3.55 (m, 4H), 3.75 (d, 2H), 6.65 (broad s, 1H), 7,40 (m, 3H), 7.55 (m, 2H), 7.65 (m, 2H), 7.70 (d, 1H), 8.25 (s, 1H) 8.32 (broad s, 1H), 9.85 (broad s, 1H).

Pharmacological Testing

The compounds of the invention have been tested using well recognised and reliable methods. The tests are as follows:

Inhibition of $^3$H-Prazosin Binding to $\alpha_1$-Adrenoceptors in Rat Brain in vitro By this method the inhibition by drugs of the binding of 3H-prazosin (0.25 nM) to $\alpha_1$-adrenoceptors in membranes from rat brain is determined in vitro. Method and results in Hyttel & Larsen, J. Neurochem. 1985, 44, 1615–1622: Skarsfeldt & Hyttel, Eur. J. Pharmacol. 1986, 125, 323–340; Hyttel & Larsen, In: Research advances in New Psychopharmacological Treatments for Alcoholism (eds. Naranjo & Sellers). Elsevier 1985, pp. 107–119.

Procedure

Male Wistar (Mol:Wist) rats (125–250 g) are sacrificed and brain tissue is dissected and weighed. The tissue is homogenized (Ultra Turrax, 10 se) in 10 mL of ice cold 50 mM tris buffer pH 7.7 (at 25° C.). The homogenate is centrifuged twice at 20,000 g for 10 min at 4° C. with rehomogenization of the pellet in 10 ml icecold buffer. The final pellet is homogenized in 250 vol (w/v) icecold buffer.

Incubation tubes (96 deep-well titer plate) kept on ice receive 50 mL of drug solution in water (or water for total binding) and 50 mL of $^3$H-prazosin (final concentration 0.25 nM). The binding experiment is initiated by addition of 1000 mL of tissue suspension (final tissue content corresponds to 3 mg original tissue) and by placing the 96 deep well titer plate in a 25 ° C. water bath. All tests are made in triplicates. After incubation for 20 min, the samples are filtered on a Brandel harvester under vacuum (18 inch. Hg) through printed filtermat B (13 mm). Titerplates and filter are washed 1×10 sec flow 50 L/h with ice cold buffer.

The filter mat is dried for 1 h at 110° C. and then placed in a sample bag with Meltilex B/HS (14.5 g) and melted together on the T-Tray heat sealer. Radioactivity is determined by counting in the 1205 Beta-plate scintillation counter (Wallac).

Specific binding is obtained by subtracting nonspecific binding estimated in the presence of 1 mM of prazosin.

For determination of the inhibition of binding, five concentrations of drugs covering 3 decades are used.

The IC$_{50}$-value is determined as the concentration at which the binding is 50% of the total binding in control samples minus the nonspecific binding in the presence of 1 mM of prazosin.

$^3$H-prazosin from New England Nuclear (TRK 647; 0.37–1.1 TBq/mmol).

Inhibition of $^3$H-Ketanserin Binding to Serotonin S$_2$ (5-HT$_{2A}$) Receptors in Rat Cortex in vitro By this method the inhibition by drugs of the binding of $^3$H-ketanserin (0.5 nM) to serotonin S$_2$ (5-HT$_2$) receptors in membranes from rat cortex is determined in vitro. Method in Hyttel, Pharmacology & Toxicology 1987, 61, 126–129:

Procedure

Male Wistar (Mol:Wist) rats (125–250 g) are sacrificed and cortical tissue is dissected and weighed. The tissue is homogenized (Ultra Turrax, 10 sec) in 10 mL of ice cold 50 mM tris buffer pH 7.7 (at 25° C.). The centrifuge glassware used in this step has been rinsed by sonication for 10 min in ethanol. The homogenate is centrifuged twice at 20,000 g for 10 min. at 4° C., with rehomogenization of the pellet in 10 mL icecold buffer. The final pellet is homogenized in 250 vol (w/v) icecold buffer.

Incubation tubes (96 deep well titer plate) kept on ice receive 50 mL of $^3$H ketanserin (final concentration 0.5 nM).

The binding experiment is initiated by addition of 1000 mL of tissue suspension (final tissue content corresponds to 4 mg original tissue) and by placing the 96 deep well titer plate in a 37° C. water bath. All tests are made in triplicates.

After incubation for 30 min, the samples are filtered on a Brandel harvester under vacuum (18 inch. Hg) through printed filter mat B (13 mm). Titerplate and filter are washed 2×10 sec. flow 50 L/h with ice cold buffer.

The printed filter mat with purred labelled tissue are dried for 1 h at 110° C. and hereafter placed in a sample bag with Meltilex B/HS 14.5 g and melted together on the T-tray heat seal. Radioactivity is determined by counting in the 1205 beta-plate scintillation counter (Wallac).

Specific binding is obtained by subtracting the nonspecific binding in the presence of 1 mM mianserin.

For determination of the inhibition of binding, five concentrations of drugs covering 3 decades are used.

The IC$_{50}$-value is determined as the concentration at which the binding is 50% of the total binding in control samples minus the nonspecific binding in the presence of 1 mM mianserin.

$^3$H-ketanserin=(ethylene-$^3$H)-ketanserin hydrochloride from New England Nuclear, specific activity 60–80 Ci/mmol.

Inhibition of $^3$H-Spiperone Binding to Dopamine D$_2$ Receptors in Rat Corpus Striatum in vitro By this method, the inhibition by drugs of the binding of $^3$H -spiperone (=$^3$H-spiro-peridol) (0.5 nM) to dopamine D-2 receptors in membranes from rat corpus striatum is determined in vitro. Method and results in Hyttel, J. Acta. Pharmacol. Toxicol. 1986, 59, 387. This is a test for dopamine D$_2$ receptor binding affinity in vitro.

Procedure

Male Wistar (Mol:Wistar) rats (125–250 g) are sacrificed and striatal tissue is dissected and weighed. The tissue is homogenized (Ultra Turrax, 10 sec.) in 10 mL of ice-cold 50 mM K-phosphate buffer pH 7.4 (at 25° C.). The homogenate is centrifuged twice at 20,000 g for 10 min at 4° C. with rehomogenization of the pellet in 10 mL ice-cold buffer. The final pellet is homogenized in 1300 vol (w/v) ice-cold buffer.

Incubation tubes kept on ice in triplicate receive 100 μl of drug solution in water (or water for total binding) and 4000 pi of tissue suspension (final tissue content corresponds to 3.08 mg original tissue). The binding experiment is initiated by addition of 100 μl of $^3$H-spiperone (final concentration 0.5 nM) and by placing the tubes in a 37° C. water bath. After incubation for 10 min, the samples are filtered under vacuum (0–50 mBar) through Whatman GF/F filters (25 mm). The tubes are rinsed with 5 mL ice-cold buffer which are then poured on the filters. Thereafter, the filters are washed with 2×5 mL of buffer. The filters are placed in counting vials and 4 mL of appropriate scintillation fluid (e.g. Picofluor ™15) are added. After shaking for 1 h and storage for 2 hrs in the dark, the content of radioactivity is determined by liquid scintillation counting. Specific binding is obtained by subtracting the nonspecific binding in the presence of 10 μM of 6,7-ADTN.

For determination of the inhibition of binding, five concentrations of drugs covering 3 orders of magnitude are used.

The $IC_{50}$, value is determined as the concentration at which the binding is 50% of the total binding in control samples minus the nonspecific binding in the presence of 10 μM of 6,7-ADTN. $^3$H-Spiperone=[phenyl-4-$^3$H]-spiperone from Amersham International plc. England, specific activity 15–25 Ci/mmol.

The results obtained are presented in table 1 below:

TABLE 1

| Compound | $IC_{50}$ values in nM | | |
|---|---|---|---|
| | $\alpha_1$ | $D_2$ | $5\text{-}HT_{2A}$ |
| Sertindole | 3.4 | 4.1 | 0.39 |
| Prazosin | 0.36 | 11000 | 3300 |
| 5a | 12 | >100 | >100 |
| 6a | 18 | >100 | >100 |
| 7a | 44 | 490 | 410 |
| 14a | 0.96 | 140 | 47 |
| 17a | 4.0 | 20 | 70 |
| 17b | 4.9 | 97 | 450 |
| 21b | 9.4 | 14 | >100 |
| 22a | 1.5 | 37 | 210 |
| 22b | 0.75 | 4.7 | 38 |
| 22c | 7.8 | 110 | >100 |
| 22d | 0.72 | 5.0 | 18 |
| 22e | 1.5 | 8.6 | 5.0 |
| 22g | 3.7 | 28 | 94 |
| 22i | 6.3 | 51 | 22 |
| 23a | 6.1 | >100 | 53 |
| 23b | 7.1 | >100 | >100 |
| 23c | 0.5 | 3.7 | 8.3 |
| 23d | 0.09 | 9.6 | 0.9 |
| 23e | 0.72 | 450 | 220 |
| 23f | 3.1 | 100 | 62 |
| 23g | 24 | >100 | 110 |
| 23h | 5.7 | >100 | 18 |

The $IC_{50}$ values for compounds of the present invention, a closely related compound, sertindole, and a well known ($\alpha_1$-antagonist, prazosin, are presented in Table 1. It is very clear that the compounds of the invention have high affinity for $\alpha_1$-adrenoceptors.

As mentioned above, the compounds of the invention have selectivity for $\alpha_1$-adrenoceptors compared to related compounds such as sertindole.

Accordingly, the affinity of the compounds of the invention for two receptors, namely dopamine $D_2$ and the $5\text{-}HT_{2A}$ receptor, for which related compounds such as sertindole have high affinity, has been determined.

It is very clear that compared to sertindole, the compounds of the invention are highly selective for the $\alpha_1$-adrenoceptor.

Testing of compounds of the invention for their ability to antagonize isoniazide induced convulsions (Christensen and Larsen, Pol. J. Pharmacol. 1982, 34, 127–134 demonstrate that the compounds have good CNS penetration. The antagonistic effect of compounds of the invention as regards the $\alpha_1$-adrenoceptors has been measured in the phenylephrine assay (R. E. Shipley and J. H. Tilden, Proc. Soc. Exper. Biol. Med. 1947, 64, 453455.

Pharmaceutical Compositions

The pharmaceutical compositions of this invention or those which are manufactured in accordance with this invention may be administered by any suitable route for example orally in the form of tablets, capsules, powders, syrups, etc., or parenterally in the form of solutions for injection. For preparing such compositions, methods well known in the art may be used, and any pharmaceutically acceptable carriers, diluents, excipients, or other additives normally used in the art may be used.

Conveniently, the compounds of the invention are administered in unit dosage form containing said compounds in an amount of about 0.01 to 100 mg.

The total daily dose is usually in the range of about 0.05–500 mg, and most preferably about 0.1 to 50 mg of the active compound of the invention.

Formulation Examples

The pharmaceutical formulations of the invention may be prepared by conventional methods in the art.

For example: Tablets may be prepared by mixing the active ingredient with ordinary adjuvants and/or diluents and subsequently compressing the mixture in a conventional tabletting machine. Examples of adjuvants or diluents comprise: corn starch, potato starch, talcum, magnesium stearate, gelatine, lactose, gums, and the like. Any other adjuvants or additives usually used for such purposes such as colourings, flavourings, preservatives etc. may be used provided that they are compatible with the active ingredients.

Solutions for injections may be prepared by dissolving the active ingredient and possible additives in a part of the solvent for injection, preferably sterile water, adjusting the solution to desired volume, sterilisation of the solution and filling in suitable ampules or vials. Any suitable additive conventionally used in the art may be added, such as tonicity agents, preservatives, antioxidants, etc.

Typical examples of recipes for the formulation of the invention are as follows:

1) Tablets containing 5.0 mg of a compound of the invention calculated as the free base:

| | |
|---|---|
| Compound of the invention | 5.0 mg |
| Lactose | 60 mg |
| Maize starch | 30 mg |
| Hydroxypropylcellulose | 2.4 mg |
| Microcrystalline cellulose | 19.2 mg |
| Croscarmellose Sodium Type A | 2.4 mg |
| Magnesium stearate | 0.84 mg |

2) Tablets containing 0.5 mg of a compound of the invention calculated as the free base:

| | |
|---|---|
| Compound of the invention | 0.5 mg |
| Lactose | 46.9 mg |
| Maize starch | 23.5 mg |
| Povidone | 1.8 mg |
| Microcrystalline cellulose | 14.4 mg |
| Croscarmellose Sodium Type A | 1.8 mg |
| Magnesium stearate | 0.63 mg |
| Syrup containing per millilitre: | |
| Compound of the invention | 25 mg |
| Sorbitol | 500 mg |
| Hydroxypropylcellulose | 15 mg |
| Glycerol | 50 mg |
| Methyl-paraben | 1 mg |
| Propyl-paraben | 0.1 mg |
| Ethanol | 0.005 ml |

| | |
|---|---|
| Flavour | 0.05 mg |
| Saccharin sodium | 0.5 mg |
| Water | ad 1 mL |
| Solution for injection containing per millilitre: | |
| Compound of the invention | 0.5 mg |
| Sorbitol | 5.1 mg |
| Acetic Acid | 0.05 mg |
| Saccharin sodium | 0.5 mg |
| Water | ad 1 mL |

What is claimed is:

1. A compound having the formula

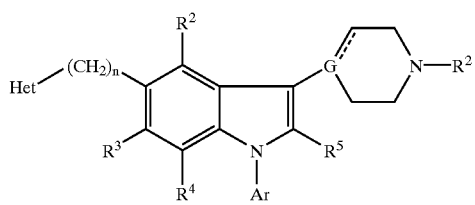

I wherein

Het is selected from the group consisting of pyrrol-1-yl, pyrrol-2-yl, pyrrol-3-yl, imidazol-1-yl, imidazol-2-yl, imidazol-4-yl, pyrazol-1-yl, pyrazol-3-yl, pyrazol-4-yl, 1,2,3-triazol-1-yl, 1,2,3-triazol-2-yl, 1,2,3-triazol-4-yl, 1,2,4-triazol-1-yl, 1,2,4-triazol-3-yl, 1,2,4-triazol-5-yl, tetrazol-1-yl, tetrazol-2-yl, tetrazol-5-yl, isoxazol-3-yl, isoxazol-4-yl, isoxazol-5-yl, isothiazol-3-yl, isothiazol-4-yl, isothiazol-5-yl, 1,2,3-oxadiazol-4-yl, 1,2,3-oxadiazol-5-yl, 1,2,4-oxadiazol-3-yl, 1,2,4-oxadiazol-5-yl, 1,3,4-oxadiazol-2-yl, 1,3,4-oxadiazol-5-yl, 1,2,3-thiadiazol-4-yl, 1,2,3-thiadiazol-5-yl, 1,2,4-thiadiazol-3-yl, 1,2,4-thiadiazol-5-yl, 1,3,4-thiadiazol-2-yl, 1,3,4-thiadiazol-5-yl, 1,2,5-oxadiazol-3-yl, 1,2,5-thiadiazol-3-yl, oxatriazol-4-yl, thiatriazol-4-yl, pyridin-2-yl, pyridin-3-yl, pyridin-4-yl, pyrimidin-2-yl, pyrimidin-4-yl, pyrimidin-5-yl, pyridazine-3-yl, pyridazine-4-yl, pyrazine-2-yl, 1,2,3-triazine-4-yl, 1,2,3-triazine-5-yl, 1,2,4-triazine-3-yl, 1,2,4-triazine-5-yl, 1,2,4-triazine-6-yl, 1,3,5-triazine-2-yl and 1,2,4,5-tetrazine-3-yl, and optionally substituted with one or more substituents selected from $C_{1-6}$-alkyl, $C_{1-6}$-alkoxy, $C_{1-6}$alkylthio and hydroxy;

n is 0, or 1;

G is N, C, or CH; the dotted line meaning a bond when G is C, and the dotted line meaning no bond when G is CH, or N;

Ar is phenyl optionally substituted with one or more substituents independently selected from halogen, $C_{1-6}$-alkyl, $C_{1-6}$-alkoxy, hydroxy, trifluoromethyl and cyano, or Ar is 2-thienyl, 3-thienyl, 2-furanyl, 3-furanyl, 2-thiazolyl, 2-oxazolyl, 2-imidazolyl, 2-pyridyl, 3-pyridyl, or 4-pyridyl;

$R^2$, $R^3$, $R^4$ and $R^5$ are independently selected from hydrogen, $C_{1-6}$-alkyl, $C_{1-6}$-alkoxy, hydroxy, halogen, trifluoromethyl, nitro, cyano, amino, $C_{1-6}$-alkylamino and $C_{1-6}$-dialkylamino;

$R^6$ is hydrogen, $C_{3-8}$-cycloalkyl, $C_{3-8}$-cycloalkyl-$C_{1-6}$-alkyl, $C_{1-6}$-alkyl, or $C_{1-6}$-alkenyl, optionally substituted with one or two hydroxy groups, any hydroxy group present being optionally esterified with an aliphatic carboxylic acid having from two to twenty-four carbon atoms inclusive, or $R^6$ is a group of the Formula II or III:

II

III wherein m is an integer from 2–6;

W is O, or S;

U is N or CH;

Z is —$(CH_2)_p$—, p being 2 or 3, or Z is —CH=CH— or 1,2-phenylene optionally substituted with halogen or trifluoromethyl, or Z is —$COCH_2$— or —$CSCH_2$—;

V is O, S, $CH_2$, or $NR^9$, wherein $R^9$ is hydrogen, $C_{1-6}$-alkyl or $C_{2-6}$-alkenyl optionally substituted with one or two hydroxy groups, or a $C_{3-8}$-cycloalkyl or $C_{3-8}$-cycloalkyl-$C_{1-6}$-alkyl group; X is N, C, or CH; Y is N, C, or CH; provided at least one of X and Y is N; and $R^7$ is hydrogen, or $C_{1-6}$-alkyl;

or a pharmaceutically acceptable acid addition salt thereof.

2. A compound according to claim 1, wherein Het is 1-alkyl-tetrazol-5-yl, 2-alkyl-tetrazol-5-yl, 1-alkyl-1,2,3-triazol-5-yl, or 2-alkyl-1,2,3-triazol-5-yl.

3. A compound according to claim 1, which is selected from:

1-[2-[4-[5-(2-methyltetrazol-5-yl)-1-(4-pyridyl)-1H-indol-3-yl]-1,2,3,6-tetrahydro-1-pyridinyl]ethyl]-2-imidazolidinone;

1-[2-[4-[5-(2-methyltetrazol-5-yl)-1-(4-pyridyl)-1H-indol-3-yl]-1-piperidinyl]eathyl]-2-imidazolidinone;

1-[2-[4-[5-(tetrazol-5-yl)-1-(4-fluorophenyl)-1H-indol-3-yl]-1-piperidinyl]-1-piperidinyl]ethyl]-2-imidazolidinone;

1-[2-[4-[1-(4-fluorophenyl)-5-(2-methyltetrazol-5-yl)-1H-indol-3-yl]piperidin-1-yl]ethyl]-2-imidazolidinone;

1-(4-fluorophenyl)-5-(2-methyltetrazol-5-yl)-3-[1-[2-(2-methyltetrazol-5-yl)ethyl]-1,2,3,6-tetrahydropyridin-4-yl]-1H-indole;

1-(4-fluorophenyl)-5-(2-methyltetrazol-5-yl)-3-[1-[2-(1-methyltetrazol-5-yl)ethyl]-1,2,3,6-tetrahydropyridin-4-yl]-1H-indole;

5-[1-(4-fluorophenyl)-3-(1-methyl-1,2,3,6-tetrahydropyridin-4-yl)-5-(2-methyltetrazol-5-yl)-1H-indole;

1-[2-[4-[1-(4-fluorophenyl)-5-(2-methyltetrazol-5-yl)-1H-indol-3-yl]-1,2,3,6-tetrahydropyridin-1-yl]ethyl]-2-imidazolidinone;

1-[2-[4-[1-(4-fluorophenyl)-5-(1-methyltetrazol-5-yl)-1H-indol-3-yl]-1,2,3,6-tetrahydropyridin-1-yl]ethyl]-2-imidazolidinone;

1-[2-[4-[5-(2-ethyltetrazol-5-yl-1-(4-fluorophenyl)-1H-indol-3-yl]-1,2,3,6-tetrahydropyridin-1-yl]ethyl]-2-imidazolidinone;

1-[2-[4-[1-(4-fluorophenyl)-5-[(1-methyltetrazol-5-yl)methyl]-1H-indol-3-yl]-1,2,3,6-tetrahydropyridin-1-yl]ethyl]-2-imidazolidinone;

1-[2-[4-[1-(4-fluorophenyl)-5-[(2-methyltetrazol-5-yl)methyl]-1H-indol-3-yl]-1,2,3,6-tetrahydropyridin-1-yl]ethyl]-2-imidazolidinone;

1-[2-[4-[1-(4-fluorophenyl)-5-(1-methyltriazol-4-yl)-1H-indol-3-yl]-1,2,3,6-tetrahydropyridin-1-yl]ethyl]-2-imidazolidinone;

1-[2-[4-[1-(4-fluorophenyl)-5-(2-methyltriazol-4-yl)-1H-indol-3-yl]-1,2,3,6-tetrahydropyridin-1-yl]ethyl]-2-imidazolidinone;

1-[2-[4-[5-(2-ethyltriazol-4-yl)-1-(4-fluorophenyl)-1H-indol-3-yl]-1-1,2,3,6-tetrahydropyridin-1-yl]ethyl]-2-imidazolidinone;

1-[2-[4-[5-(2-ethyltetrazol-5-yl)-1-(4-fluorophenyl)-1H-indol-3-yl]-1-piperidinyl]ethyl]-2-imidazolidinone;

1-(4-fluorophenyl)-3-(1-methyl-4-piperidinyl)-5-(2-methyltetrazol-5-yl)-1H-indole;

1-[2-[4-[(1-(4-fluorophenyl)-5-[(1-methyltetrazol-5-yl) methyl]-1H-indol-3-yl]-1-piperidinyl]ethyl]-2-imidazolidinone;

1-[2-[4-[1-(4-fluorophenyl)-5-[(2-methyltetrazol-5-yl) methyl]-1H-indol-3-yl]-1-piperidinyl]ethyl]-2-imidazolidinone;

1-[2-[4-[1-(4-fluorophenyl)-5-(1-methyltriazol-4-yl)-1H-indol-3-yl]-1-piperidinyl]ethyl]-2-imidazolidinone;

1-[2-[4-[1-(4-fluorophenyl)-5-(2-methyltriazol-4-yl)-1H-indol-3-yl]-1-piperidinyl]ethyl]-2-imidazolidinone;

1-[2-[4-[5-(1-ethyltriazol-4-yl)-1-(4-fluorophenyl)-1H-indol-3-yl]-1-piperidinyl]ethyl]-2-imidazolidinone; and 1-[2-[4-[5-(2-ethyltriazol-4-yl)-1-(4-fluorophenyl)-1H-indol-3-yl]-1-piperidinyl]ethyl]-2-imidazolidinone;

or a pharmaceutically acceptable acid addition salt thereof.

4. A compound according to claim 1 which is radiolabelled.

5. A pharmaceutical composition comprising at least one compound according to claim 1 or a pharmaceutically acceptable acid addition salt thereof in combination with one or more pharmaceutically acceptable carrier or diluents.

6. A method for the treatment of a disorder or disease responsive to antagonism of a $\alpha_1$-adrenoceptors in a mammal in need thereof comprising administering an $\alpha_1$-adrenoceptors antyagonizing amount of a compound according to claim 1 or an acid addition salt thereof to said mammal.

7. A method for the treatment of psychosis in a mammal in need thereof comprising administering a therapeutically effective amount of a compound according to claim 1 or an acid addition salt thereof to said mammal.

8. A compound according to claim 4 which is radiolabeled with [$^{11}$C]-methyl.

* * * * *